United States Patent
Crawford

(10) Patent No.: US 8,500,690 B2
(45) Date of Patent: *Aug. 6, 2013

(54) PASSIVELY SHIELDING NEEDLE DEVICE

(75) Inventor: Jamieson Crawford, Cliffside Park, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1289 days.

This patent is subject to a terminal disclaimer.

(21) Appl. No.: 11/909,879

(22) PCT Filed: Jul. 1, 2005

(86) PCT No.: PCT/US2005/023515
§ 371 (c)(1),
(2), (4) Date: Sep. 27, 2007

(87) PCT Pub. No.: WO2006/007556
PCT Pub. Date: Jan. 19, 2006

(65) Prior Publication Data
US 2008/0306452 A1    Dec. 11, 2008

Related U.S. Application Data

(63) Continuation-in-part of application No. 10/882,659, filed on Jul. 1, 2004, now Pat. No. 7,201,740.

(51) Int. Cl.
*A61M 5/00* (2006.01)

(52) U.S. Cl.
USPC ............................................ 604/110

(58) Field of Classification Search
USPC ............ 604/110, 192–198, 263, 181, 171, 604/164.08, 165.03, 240
See application file for complete search history.

(56) References Cited

U.S. PATENT DOCUMENTS

| | | |
|---|---|---|
| 5,085,639 A | 2/1992 | Ryan |
| 5,088,982 A | 2/1992 | Ryan |
| 5,112,311 A | 5/1992 | Utterberg et al. |
| 5,120,320 A | 6/1992 | Fayngold |
| 5,154,699 A | 10/1992 | Ryan |
| 5,176,655 A | 1/1993 | McCormick et al. |
| 5,186,712 A | 2/1993 | Kelso et al. |
| 5,192,275 A | 3/1993 | Burns |
| 5,266,072 A | 11/1993 | Utterberg et al. |
| 5,290,264 A | 3/1994 | Utterberg et al. |

(Continued)

*Primary Examiner* — Matthew F Desanto
(74) *Attorney, Agent, or Firm* — The Webb Law Firm

(57) ABSTRACT

A shieldable needle device includes a hub with and a needle cannula having a puncture tip extending from a forward end thereof, and a shield member in telescoping association with the hub. At least one of the hub and the shield member are adapted for relative axial movement with respect to the other between a first position in which the puncture tip of the needle cannula is exposed from a forward end of the shield member and a second position in which the puncture tip of the needle cannula is encompassed within the shield member. A drive member extends between the hub and the shield member, biasing the hub and the shield member axially away from each other. A packaging cover may further extend about the needle cannula, applying external pressure between the cooperating portions of the hub and the shield. In use, external pressure is applied by a user to at least one of the hub and the shield member providing an engagement therebetween, thus permitting removal of the packaging cover and preventing the drive member from biasing the hub and the shield member axially away from each other until activation is desired.

25 Claims, 28 Drawing Sheets

U.S. PATENT DOCUMENTS

| | | |
|---|---|---|
| 5,300,039 A | 4/1994 | Poulsen |
| 5,429,611 A * | 7/1995 | Rait ............................. 604/197 |
| 5,562,636 A | 10/1996 | Utterberg et al. |
| 5,562,637 A | 10/1996 | Utterberg et al. |
| 5,746,726 A | 5/1998 | Sweeney et al. |
| 5,779,679 A | 7/1998 | Shaw |
| 5,951,525 A | 9/1999 | Thorne et al. |
| RE36,398 E | 11/1999 | Byrne et al. |
| RE36,447 E | 12/1999 | Byrne et al. |
| 6,537,259 B1 | 3/2003 | Niermann |
| 6,659,983 B2 | 12/2003 | Crawford et al. |
| 7,201,740 B2 * | 4/2007 | Crawford ...................... 604/198 |
| 2002/0099339 A1 * | 7/2002 | Niermann ..................... 604/263 |
| 2003/0078540 A1 | 4/2003 | Saulenas et al. |
| 2003/0135157 A1 | 7/2003 | Saulenas et al. |
| 2003/0144632 A1 * | 7/2003 | Hommann et al. ........... 604/198 |
| 2003/0181869 A1 | 9/2003 | Swenson et al. |
| 2003/0181871 A1 | 9/2003 | Wilkinson et al. |
| 2004/0010227 A1 | 1/2004 | Riesenberger et al. |
| 2005/0119627 A1 | 6/2005 | Crawford |

\* cited by examiner

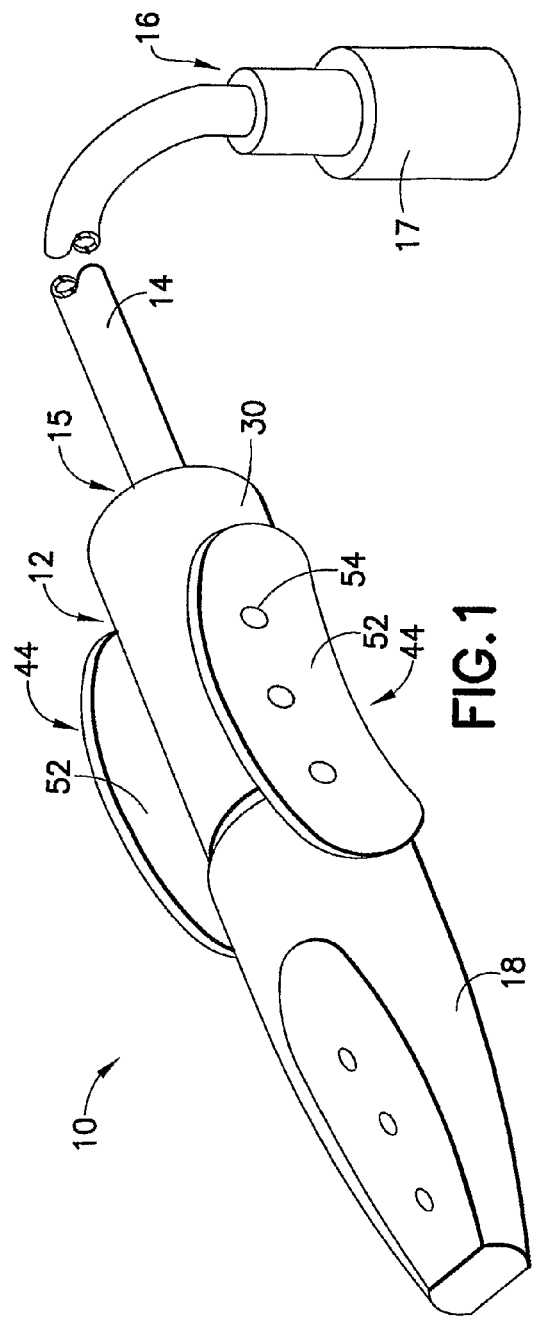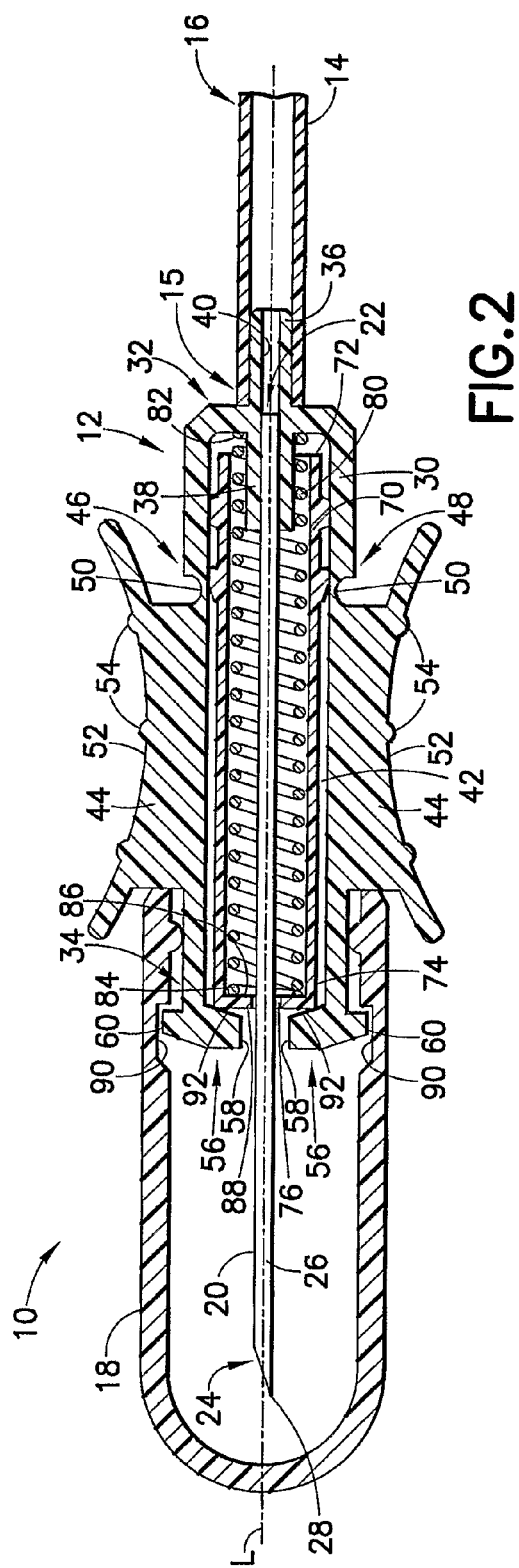

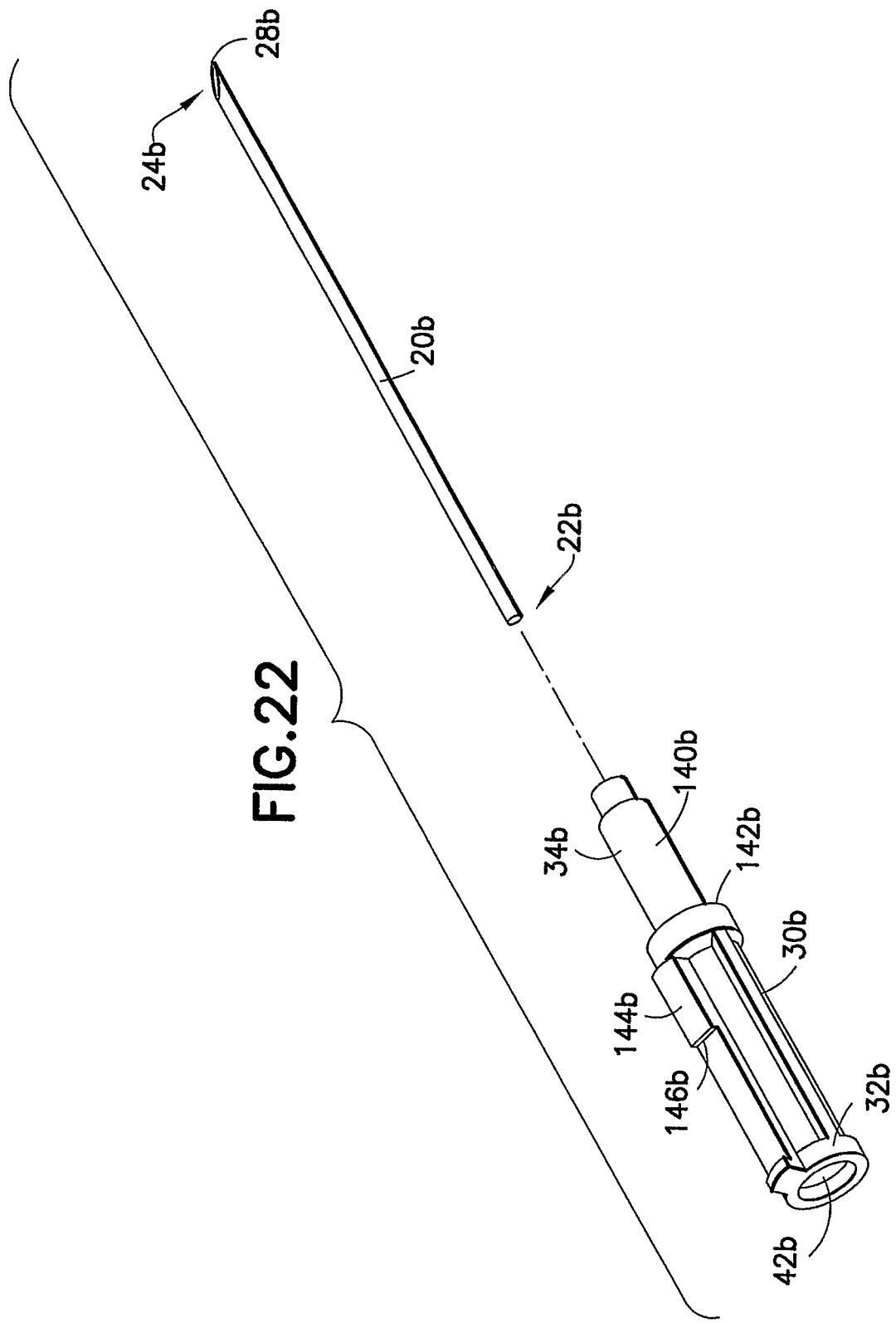

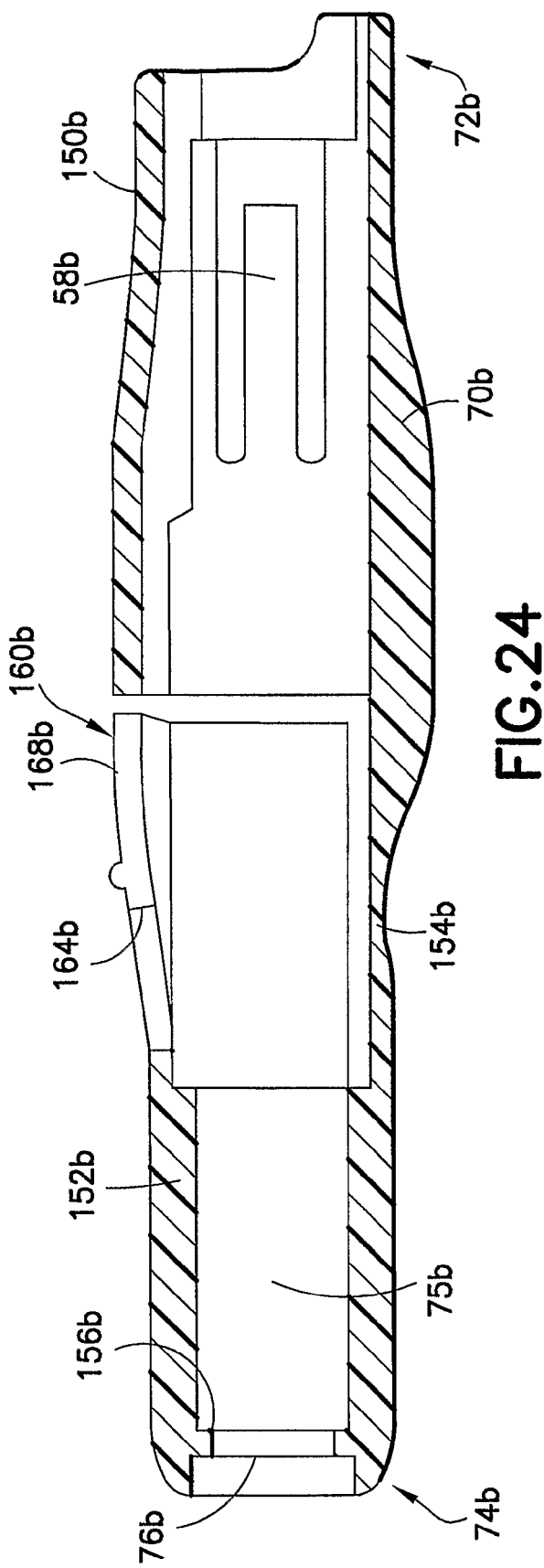

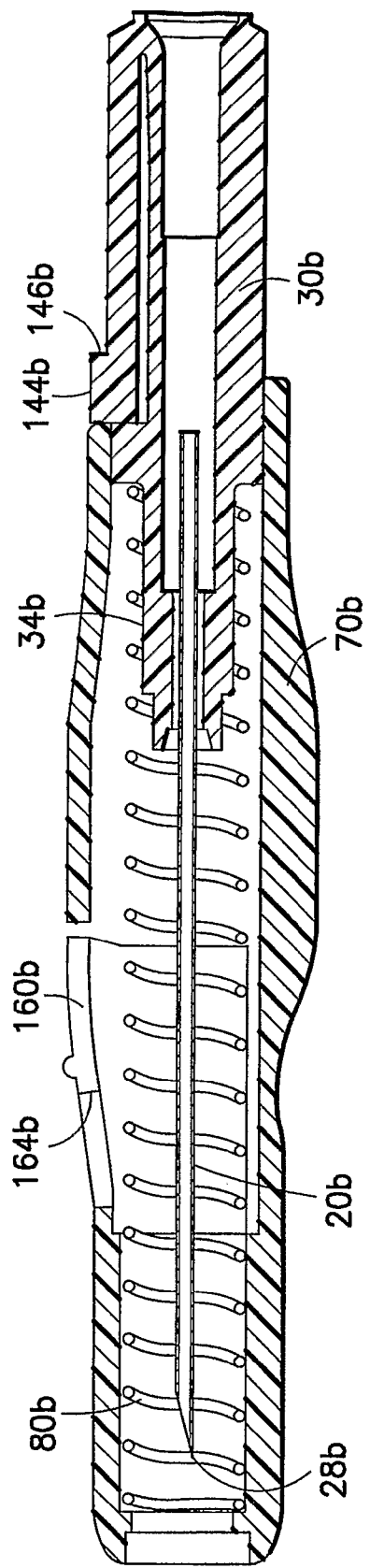

PASSIVELY SHIELDING NEEDLE DEVICE

BACKGROUND OF THE INVENTION

1. Field of the Invention

The present invention relates to a needle assembly including a needle safety shield for protecting users from a used needle tip, such as for use in a blood collection set for safe and convenient handling of needles used in blood collection procedures.

2. Description of Related Art

Disposable medical devices having medical needles are used for administering medication or withdrawing fluid from the body of a patient. Such disposable medical devices typically include blood collecting needles, fluid handling needles, and assemblies thereof. Current medical practice requires that fluid containers and needle assemblies used in such devices be inexpensive and readily disposable. Existing blood collection devices often employ some form of durable holder onto which disposable medical needles and fluid collection tubes may be mounted. A blood collection device of this nature may be assembled prior to use and then discarded after use.

A blood collection device or intravenous (IV) infusion device typically includes a needle cannula having a proximal end, a pointed distal end, and a lumen extending therebetween. The proximal end of the needle cannula is securely mounted in a plastic hub defining a central passage that communicates with the lumen extending through the needle cannula. A thin, flexible thermoplastic tube is connected to the hub and communicates with the lumen of the needle cannula. The end of the plastic tube remote from the needle cannula may include a fixture for connecting the needle cannula to a holder or other receptacle. The specific construction of the fixture will depend upon the characteristics of the receptacle to which the fixture is to be connected.

In order to reduce the risk of incurring an accidental needle-stick wound, protection of used needle cannulas becomes important. With concern about infection and transmission of diseases, methods and devices to enclose or cover the used needle cannula have become very important and in great demand in the medical field. For example, needle assemblies often employ a safety shield that can be moved into shielding engagement with a used needle cannula to minimize risk of an accidental needle stick.

Some needle safety shields are referred to as "tip guards" and include a small rigid guard that may be telescoped along the length of the needle cannula and extended over the pointed distal end of the needle cannula for protection. Such conventional tip guards may include some form of tether for limiting the travel of the tip guard to the length of the needle cannula. An example of the foregoing is disclosed by U.S. Pat. No. 5,176,655 to McCormick et al. The McCormick et al. patent discloses the use of flexible loop-like straps for limiting the distal movement of a tip guard.

Needle shields that incorporate movable tip guards are typically manually actuated. For example, U.S. Pat. Nos. Re. 36,447 and Re. 36,398, both to Byrne et al., disclose a safety device for a hypodermic needle that includes a plastic sheath, which is used to cover the puncture tip of the needle. The plastic sheath incorporates a thumb guard, which the user of the safety device may grasp to move the plastic sheath to a position covering the puncture tip of the needle. U.S. Pat. No. 5,951,525 to Thorne et al. discloses a manually operated safety needle apparatus that includes two pairs of opposed legs adapted to move the tip guard of the apparatus to a position covering the used needle cannula. U.S. Pat. Nos. 5,562,637 and 5,562,636, both to Utterburg, disclose a rectangular needle protector sheath for use with a needle cannula that may be extended over the needle cannula after it is used. Other prior art devices, such as those disclosed by U.S. Pat. Nos. 5,290,264 to Utterberg and 5,192,275 to Burns, provide "grippable" members attached to the tip guards to facilitate moving the tip guards to a position covering the puncture tip of a needle cannula. In addition to providing gripping members for moving the tip guards, prior art devices in this area often include flexible wings, which are used as means for securing the needle assemblies to the body of a patient during a medical procedure. Examples of "winged" needle assemblies may be found in U.S. Pat. Nos. 5,120,320 to Fayngold; and 5,154,699; 5,088,982; and 5,085,639 all to Ryan. Other prior art in this area includes U.S. Pat. Nos. 5,266,072 and 5,112,311, both to Utterberg et al., which also disclose guarded winged needle assemblies.

U.S. Patent Application Publication No. 2002/0099339 to Niermann discloses a passive safety blood collection set which includes a tip guard slidably movable along a needle cannula. The tip guard is mounted to a needle hub through a pair of collapsible leaves, which are collapsed onto themselves and held in place by a packaging cover. In use, the practitioner holds the leaves in the collapsed or folded state to remove the cover, and then releases the leaves enabling them to unfold to propel the tip guard distally.

Conventional tip guards, such as those discussed hereinabove, often include a structure that lockingly engages over the pointed distal end of the used needle cannula to prevent a re-exposure of the needle cannula. The structure for preventing the re-exposure of the needle cannula may include a metallic spring clip or a transverse wall formed integrally with one end of the tip guard. An example of a metallic spring clip is disclosed by the McCormick et al. patent discussed previously. Conventional tip guards, such as those discussed hereinabove, often further require extensive mechanics for positioning the tip guard over the needle cannula. This results in complex arrangements that are costly to manufacture and assemble. Additionally, operation of the needle assemblies to move the tip guard into the proper position over the pointed distal end of the needle cannula requires substantial manual manipulation by the user of the device, exposing the user to potential needle-stick wounds.

U.S Patent Application Publication No. 2003/0078540 to Saulenas et al. discloses a retractable push button needle assembly, in which a needle is attached to a hub and extends through a barrel. A push button actuator extends from the hub and is in interference engagement with the barrel. Activation is accomplished with a user actively pushing the push button into the barrel, thereby causing the needle to retract within the barrel based on a spring disposed between the hub and the barrel.

SUMMARY OF THE INVENTION

A need exists for a shielding needle assembly that achieves secure and effective shielding of a used needle cannula, and which is simple to manufacture and easy to operate. Additionally, a need exists for a needle assembly, such as for use in a blood collection set, that is passively operated during a normal blood collection procedure.

In one embodiment of the present invention, a safety needle device comprises a hub including a passageway extending therethrough and a needle cannula having a puncture tip extending from a forward end thereof. A shield member is in telescoping association with the hub, with at least one of the hub and the shield member adapted for relative telescoping movement with respect to the other between a first position in which the puncture tip of the needle cannula is exposed from a forward end of the shield member and a second position in which the puncture tip of the needle cannula is encompassed within the shield member. A drive member is disposed between the hub and the shield member, and is capable of biasing the hub and the shield member telescopically away from each other. External pressure applied by a user to at least one of the hub and the shield member provides an engagement therebetween, preventing the drive member from biasing the hub and the shield member away from each other, such as in an axial direction. For example, external pressure applied by a user between corresponding surfaces of the hub and the shield member may provide an interference engagement therebetween, preventing the drive member from biasing the hub and/or the shield member axially away from each other.

In one embodiment, the safety needle device further includes a releasable packaging cover disposed about the puncture tip of the needle cannula. The packaging cover is adapted to apply external pressure to at least one of the hub and the shield member to provide an engagement therebetween, thereby preventing the drive member from biasing the hub and the shield member axially away from each other. In this manner, application of external pressure by a user to at least one of the hub and the shield member allows for release of the packaging cover from the needle device, and maintains the engagement between the hub and the shield member to prevent the drive member from biasing the hub and the shield member axially away from each other, thus providing a passive device.

One of the hub or the shield member may include at least one release member disposed at least partially within the packaging cover which is adapted to flex radially inward toward a central longitudinal axis of the needle device upon application of external pressure thereto. In this manner, passive release of the packaging cover from the hub or the shield member can be accomplished during normal use when the needle device is grasped by a user.

In a further embodiment, a safety needle device comprises a needle cannula comprising a proximal end and a distal end with a puncture tip, a housing defining a passageway extending therethrough, with the puncture tip of the needle cannula extending from a distal end of the housing, and a packaging cover releasably disposed about the distal end of the housing and enclosing the puncture tip of the needle cannula prior to using the safety needle device. The housing comprises at least one release member disposed at least partially within the packaging cover and adapted to flex radially inward toward a central longitudinal axis of the housing upon applying external pressure thereto, allowing passive release of the packaging cover from the distal end of the housing. The at least one release member may be pivotally connected to the housing, and may include a locking tab engaging a locking groove defined within the packaging cover. In this manner, application of external pressure causes the locking tab to disengage from the locking groove to allow passive release of the packaging cover from the distal end of the housing. Desirably, the housing includes a pair of opposing release members each comprising a locking tab engaging a locking groove defined within the packaging cover. A shield member may further be provided, which is axially movable with respect to the housing and which is maintained in a retracted position against a biasing force between the housing and the shield member by external pressure applied to the release member by the packaging cover, which external pressure maintains the shield member in the retracted position in which the puncture tip of the needle cannula is exposed from the shield member. Application of external pressure to the at least one release member, such as through a user's fingers grasping the at least one release member, causes the packaging cover to release from the housing and further causes the at least one release member to continue to maintain the shield member in the retracted position against the bias. The safety needle device may further be connected to a flexible tube which is adapted for connection to a receptacle, thereby providing a blood collection assembly.

In one particular embodiment of the invention, the needle device includes a shield member which may be movably associated with a hub between a first position in which the shield member is retracted within the hub and a second position with the shield member extended for shielding the puncture tip of a needle cannula. In such an embodiment, the hub may include at least one release member pivotally connected thereto, for maintaining the shield member within the hub against a biasing force provided by a drive member, such as a coil spring. A releasable packaging cover may also be disposed about the puncture tip of the needle cannula when the shield member is in the first position retracted within the hub, with the packaging cover engaged with the at least one release member to maintain radial pressure against the at least one release member, thereby maintaining the shield member within the hub against the bias of the drive member. Application of radial pressure by a user to the at least one release member causes the at least one release member to pivot radially inward, disengaging from any packaging cover which may be present to release the packaging cover from the hub, and further causing the at least one release member to engage the shield member and maintain the shield member in the retracted position. Release of the radial pressure applied by a user releases the engagement between the at least one release member and the shield member, thereby enabling the drive member to move the shield member from the first position retracted within the hub to the second position shielding the puncture tip of the needle cannula. In such an embodiment, the at least one release member may be pivotally connected to the hub, for example, substantially at the hub proximal end. Desirably, a pair of opposing release members are pivotally connected to the hub, for example, substantially at the hub proximal end. A finger tab may be provided on each of the release members for applying the radial inwardly directed pressure to the release members. The release member may further include at least one resiliently deflectable locking member such as a locking tab adapted to engage a locking recess in the safety shield member when it is in the extended position. Further, the release member may include a locking tab engaging a locking groove in the packaging cover, generally preventing removal of the packaging cover until radial pressure is applied to the at least one release member, causing the at least one release member to pivot radially inward and disengage the locking tab from the locking groove.

In another particular embodiment, the shield member includes a forward end and a rearward end defining a passageway extending therethrough, such as a barrel, with the hub disposed within the passageway of the shield member. In such an embodiment, the hub includes a release member, such as a button protrusion, extending toward the forward end thereof, and the shield member includes at least one release tab adapted for engagement with a surface of the release member of the hub and adapted to deflect radially outwardly from the shield member out of engagement from the release member when in a relaxed, unbiased state. External pressure maintains the release tab in the biased state in interference engagement with at least a portion of the release member of the hub, thereby maintaining the hub in the first position against the bias of the drive member. Sufficient release of the external pressure from the release tab permits the release tab to move to the unbiased state out of interference engagement with the release member, allowing the drive member to move the hub toward the second position wherein the puncture tip of the needle cannula is encompassed by the shield member. Desirably, a pair of release tabs extend longitudinally from opposing lateral sides of the shield member in a rearward direction, cooperatively defining an opening for receiving the release member in the interference engagement in the biased state of the release tabs. The at least one release tab preferably extends outward from the shield member when in the relaxed, unbiased state, and is adapted to deflect radially inward for engagement with the release member of the hub when external pressure is applied thereto. In such an embodiment, the drive member, desirably a coil spring, is disposed in the shield member and is associated with the hub for moving the hub toward the proximal position of the needle device. At least one resiliently deflectable locking member may also be associated with the shield member and adapted to engage the hub when the hub substantially reaches the proximal position for preventing re-exposure of the needle cannula. For example, the shield member may further include at least one flexible cutout portion or locking tab along a wall thereof, with the flexible cut out portion biased inwardly, such that the flexible cut out portion is adapted for interfering engagement with a portion of the hub when retracted to prevent a return movement.

In yet a further particular embodiment, the hub includes a dorsal member extending from an external surface thereof, and the shield member includes a grip structure extending dorsally therefrom adapted for corresponding engagement with the dorsal member at the external surface of the hub when the shield member is in a first retracted position, thereby forming a dorsal grasping structure. External pressure applied between the grip structure of the shield member and the dorsal member of the hub prevents the drive member from biasing the hub and the shield member axially away from each other. In such an embodiment, the shield member preferably telescopes within the passageway of the hub and the grip structure extends dorsally from the shield member toward the dorsal member of the hub, such that external pressure applied between the grip structure of the shield member and the dorsal member of the hub establishes frictional engagement therebetween. The shield member is thereby maintained in a retracted position within the passageway of the hub against the bias of the drive member with the puncture tip of the needle cannula exposed. Release of the external pressure between the grip structure of the shield member and the dorsal member of the housing releases the frictional engagement, allowing the drive member to bias the shield member toward an extended position in which the puncture tip of the needle cannula is encompassed within the shield member. A packaging cover may be provided in such an embodiment for releasably covering the forward end of the puncture tip when the shield is in the retracted position. Such a protective cap may provide for external pressure between the grip structure of the shield and the dorsal member of the housing to maintain the shield in the retracted position against the bias of the drive member.

Desirably, the dorsal member of the housing comprises a generally planar spine extending dorsally from the external surface of the housing in a plane corresponding to a longitudinal axis defined by the needle cannula, and the grip structure comprises generally planar structure for corresponding engagement with the spine of the housing. For example, the grip structure may define a pair of flexibly resilient planar leafs extending from a forward end of the shield in a plane corresponding to the longitudinal axis defined by the needle cannula. The pair of planar leafs may be spaced from each other to define an opening therebetween for accommodating the spine of the housing, with the pair of planar leafs joined at a forward surface of the shield at a bridge, and with at least a portion of the shield extending coaxialy within the passageway o the housing. Moreover, the planar leafs and the spine may include corresponding structure adapted for interference engagement therebetween when external pressure is applied between the pair of planar leafs and the spine. For example, an external surface of the spine may include a detent and at least one of the pair of planar leafs may include a corresponding protuberance or protrusion extending within the opening between the pair of planar leafs for interference engagement with the detent of the spine when external pressure is applied between the pair of planar leafs and the spine.

The housing and the shield may be provided with interengaging structure for interfering engagement therebetween when the shield is in the extended position to prevent a return movement of the shield to the retracted position. For example, the housing may further include at least one flexible cutout portion along a wall thereof, with the flexible cut out portion biased inwardly toward the passageway of the housing, such that the flexible cut out portion is adapted for interfering engagement with a portion of the shield when the shield is in the extended position to prevent a return movement of the shield to the retracted position. Moreover, the housing may include a pair of wings extending laterally from opposing sides thereof. Such wings are in fixed relation to the housing, and are of a relative size and shape such that corresponding engagement of the dorsal member of the housing and the grip structure of the shield form a dorsal grasping structure when the shield is in the retracted position, with the dorsal grasping structure having a profile larger than the pair of wings on the housing.

A further embodiment involves a method of passively activating a shieldable needle device, such as one of the particular devices noted above. Such a method generally includes providing the shielding needle device including a needle cannula having a puncture tip, a hub supporting the needle cannula, a shield member in telescoping association with the hub and disposed generally coaxially with the hub, and a drive member associated with the hub and the shield member biasing the hub and the shield member axially away from each other. Additionally, the method includes applying radial pressure to one or both of the hub and the shield member, such that they engage each other, thereby preventing the drive member from biasing the hub and the shield member axially away from each other to maintain the needle device in a first position with the puncture tip exposed from the shield.

In one particular embodiment, the method involves providing the needle device including a housing having a dorsal member extending from an external surface thereof and a needle cannula having a puncture tip extending from a forward end thereof; a shield axially moveable with respect to the housing between a retracted position in which the puncture tip is exposed and biased toward an extended position covering the puncture tip, the shield including grip structure extending dorsally from an external surface thereof for corresponding engagement with the dorsal member of the housing to form a dorsal grasping element when the shield is in the retracted position; and a protective cap releasably attached to a forward end of the needle device for maintaining the shield in the retracted position against the bias and covering the puncture tip. The method further involves grasping the needle device at the dorsal grasping element applies external pressure between the grip structure of the shield and the dorsal member of the housing and removing the protective cap from the forward end of the housing. Upon release of the external pressure between the grip structure of the shield and the dorsal member of the housing, the biasing force will move the shield axially toward the extended position. The grasping step establishes frictional engagement between the grip structure of the shield and the dorsal member of the housing. The method may further include the step of preventing the shield from returning to the retracted position after moving to the extended position, such as by providing interengaging structure for interfering engagement therebetween when the shield is in the extended position to prevent a return movement of the shield to the retracted position.

Further details and advantages of the present invention will become apparent from the following detailed description when read in conjunction with the accompanying drawings.

BRIEF DESCRIPTION OF THE DRAWINGS

FIG. 1 is a perspective view of a shielding blood collection set including a needle device in accordance with an embodiment of the present invention, having a releasable packaging cover disposed at a distal end of the needle device.

FIG. 2 is a longitudinal cross-sectional view of the needle device shown in FIG. 1.

FIG. 22 is an exploded perspective view of a hub of the needle device of FIG. 20.

FIG. 24 is a side view of a shield of the needle device of FIG. 20.

FIG. 33 is a longitudinal cross-sectional similar to FIG. 32, but including the alternate hub of FIG. 23B.

DETAILED DESCRIPTION OF THE INVENTION

Figure 3:
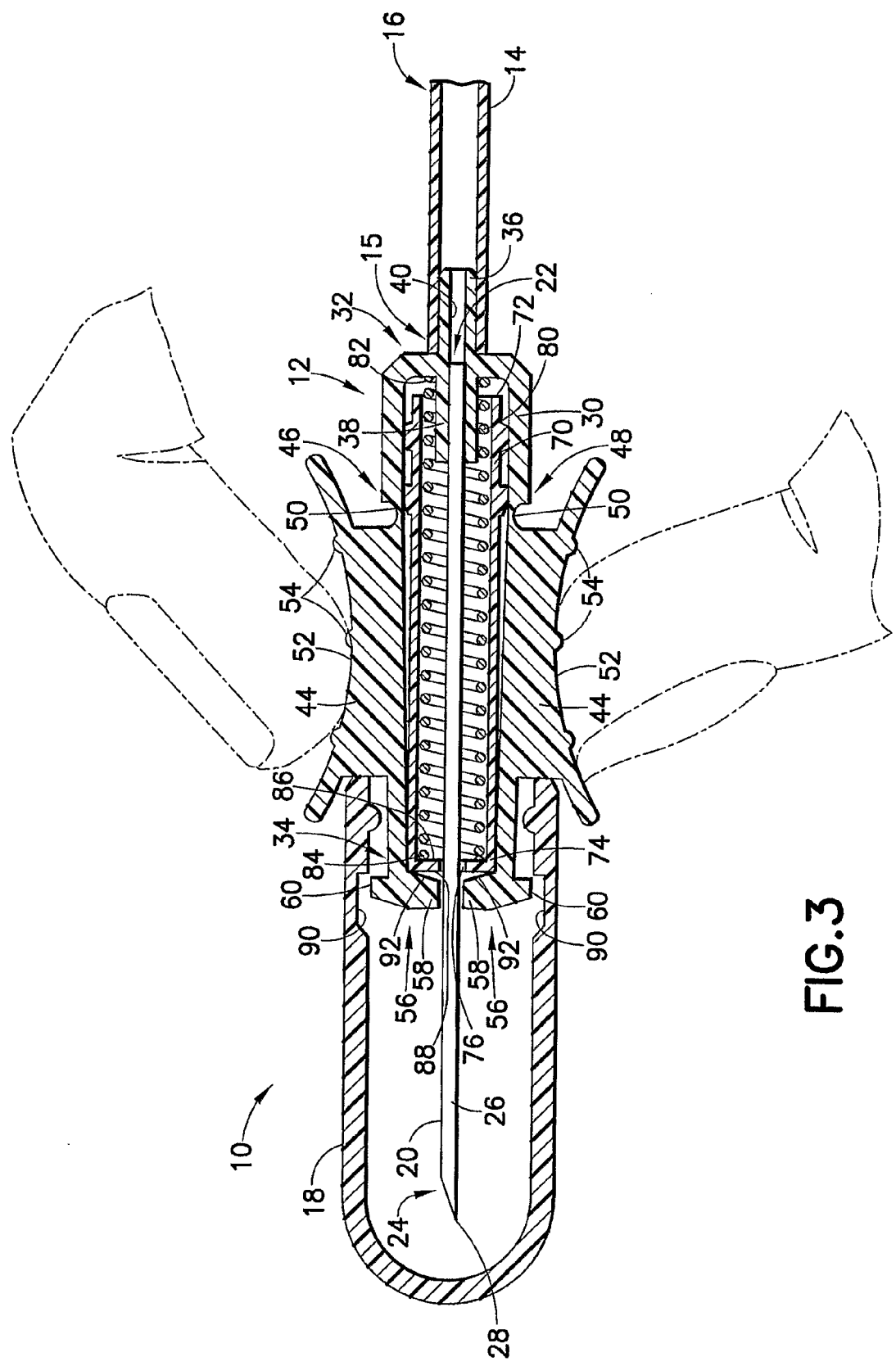
FIG. 3 is a longitudinal cross-sectional view of the needle device shown in FIG. 1, showing a user manipulating the needle device.

Referring to the drawings in which like reference characters refer to like parts throughout the several views thereof, FIG. 1 illustrates generally a blood collection set 10 in accordance with an embodiment of the present invention and its related features. The present invention is generally described herein in terms of a safety shielding needle assembly for use in a blood collection set, and encompasses a shielding needle assembly, as well as a blood collection set incorporating shielding needle assemblies. It is contemplated that the shielding needle assembly may be incorporated into other medical devices in alternate embodiments of the invention, such as intravenous assemblies, fluid infusion sets, hypodermic syringes, and the like.

As shown generally in FIG. 1, the blood collection set 10 includes a safety shielding needle device or assembly 12, a flexible tube 14 extending from the needle device or assembly 12 and having first and second ends 15, 16, and a protective cap or shield such as packaging cover 18 removably mounted to the needle assembly 12 opposite tube 14, such as through a frictional engagement. Needle assembly 12 extends from a first end 15 of flexible tube 14, while the second end 16 of flexible tube 14 is adapted for connection with a receptacle for blood collection. For example, the second end 16 of flexible tube 14 may be provided with a proximal fitting 17 which is adapted for engagement with a conventional needle holder (not shown) as is known in the art. Fitting 17 may further define a hub element including a non-patient needle assembly (not shown) as is commonly known in the art for use in blood collection sets. Alternatively, fitting 17 may define a luer connector that can be mated with an appropriate connector of a separate device as is known in the art, such as for mating with an infusion set for infusing a medication into a patient.

With general reference to FIGS. 2-8, one embodiment of the invention defines the shielding needle assembly 12 generally including a needle cannula 20, a hub 30, a needle cannula safety shield member 70, and a drive member 80 for moving the safety shield 70. The needle cannula 20 includes a rearward or proximal end 22 and an opposing forward or distal end 24, with a lumen 26 extending through needle cannula 20 from the proximal end 22 to the distal end 24. The distal end 24 of needle cannula 20 may be beveled to define a sharp puncture tip 28, such as an intravenous puncture tip. The puncture tip 28 is provided for insertion into a patient's blood vessel, such as a vein, and is therefore designed to provide ease of insertion and minimal discomfort during venipuncture. Needle cannula 20 is desirably constructed of a medical grade metallic material, such as surgical steel or the like.

The needle assembly 12 further includes a hub 30. The hub 30 is generally tubular or cylindrical in shape, and may be a unitary structure, desirably molded from a resilient thermoplastic material, or may be a multi-component structure. The hub 30 includes a rearward or proximal end 32 and a forward or distal end 34. The proximal end 32 of the hub 30 includes an external portion or structure 36 for mating with the first end 15 of the flexible tube 14, and an internal portion or structure 38 for engaging the drive member 80, which is preferably in the form of a coil spring or like element for biasing the safety shield 70 in the manner described herein. The external and internal portions or structures 36, 38 are generally tubular shaped components adapted to cooperate with the flexible tube 14 and drive member 80, respectively. The external structure 36 may be adapted to cooperate with the flexible tube 14 in a friction-fit manner, and a suitable medical grade adhesive may be used to secure the connection.

As depicted in FIGS. 2-8, the needle cannula 20 and the hub 30 may be separate parts that are preferably fixedly attached and secured through an appropriate medical grade adhesive, for example, epoxy or the like. In particular, the proximal end 22 of the needle cannula 20 is supported by the proximal end 32 of the hub 30 and, in particular, the internal structure 38 formed in the proximal end 32 of the hub 30. For this purpose, the hub 30 defines a passageway or opening 40 extending between the internal structure 38 and the external structure 36 for receiving and securing the proximal end 22 of the needle cannula 20 therein. The opening 40 preferably extends through the proximal end 32 of the hub 30 and is used to place the needle assembly 12 in fluid communication with the flexible tube 14, or another medical device, such as a tube holder, syringe, and like devices. The proximal end 22 of the needle cannula 20 may extend into the opening 40 and extend into the external structure 36 provided on the proximal end 32 of the hub 30. The needle cannula 20 is secured within the opening 40 by an appropriate medical grade adhesive, and generally extends toward the distal end of the needle assembly 12 through an internal passageway 42 extending through hub 30, with the puncture tip 28 at distal end 24 of needle cannula 20 extending through the forward or distal end 34 of hub 30.

The needle assembly 12 further includes a shield member such as safety shield 70, which extends telescopically about needle cannula 20, such as in a generally coaxial manner. The safety shield 70 is in telescoping association with the hub 30, such that at least one of hub 30 and/or shield 70 are adapted for relative movement with respect to the other in a generally axial direction, that is in a general direction with respect to the general longitudinal axis L of needle assembly 12. More particularly, the shield 70 and/or the hub 30 are telescopically movable with respect to one another between a first position of the needle assembly 12 in which the puncture tip 28 of needle cannula 20 is exposed from a forward end of the shield 70, and a second position in which the shield 70 generally encompasses the needle cannula 20 and, more particularly, the puncture tip 28, as will be described in more detail herein. The safety shield 70 is generally tubular or cylindrical in shape, and may be a unitary structure, desirably molded from a thermoplastic material, including a rearward or proximal end 72 and a forward or distal end 74. The distal end 74 defines a central opening 76 through which the needle cannula 20 extends. The central opening 76 permits relative telescopic movement between the safety shield 70 and the needle cannula 20 between the first and second positions of the needle assembly 12 noted above.

The needle assembly 12 further includes drive member 80 extending between the hub 30 and the shield 70, providing a biasing force to bias the hub 30 and the shield 70 axially or longitudinally away from each other. Drive member 80 is generally coaxially positioned with the shield 70 and/or the hub 30, with the needle assembly 12 in the first position. The drive member 80 may be in the form of a coil compression spring or like biasing element and is generally adapted to move the safety shield 70 and/or the hub 30 with respect to each other between the first position and the second position of the needle assembly 12. The drive member 80 has a proximal end 82 and a distal end 84. The proximal end 82 is generally disposed on the internal structure 38 formed internally at the proximal end 32 of the hub 30. The distal end 84 is generally in contact with a portion of the shield 70, such as an interior surface 86 defined within the distal end 74 of the safety shield 70. The biasing force of the drive member 80 is described herein in terms of biasing the hub 30 and shield 70 with respect to each other, such as a biasing force biasing the hub 30 an the shield 70 axially away from each other. It is noted that activation of the needle assembly 12 is based on this biasing force of drive member 80 causing movement of either the hub 30 or the shield 70, or movement of both the hub 30 and the shield 70 with respect to each other. For example, it the user is holding the hub 30 during activation, the biasing member 80 will cause the shield 70 to extend or move distally with respect to hub 30 to the second shielding position of needle assembly 12. On the other hand, if the user is holding the shield 70 during activation, the biasing member 80 will cause the hub 30 to retract or move proximally with respect to shield 70 to the second shielding position of the needle assembly 12.

A packaging cover 18 may also be provided on the needle assembly 12, such as at the distal end 34 of hub 30, and is preferably provided on the needle assembly 12 during the manufacturing process.

In a general sense, the hub 30 and the shield 70 are maintained from movement with respect to each other against the bias of the drive member 80 to maintain needle assembly 12 in the first position with puncture tip 28 extending from the forward end of the shield 70. The hub 30 and shield 70 may be maintained in this manner through external pressure applied externally to the structure of needle assembly 12 by a user during the normal use of needle assembly 12. Such external pressure provides an engagement between the hub 30 and the shield 70 to prevent the drive member 80 from biasing the hub 30 and the shield 70 away from each other in a longitudinal direction. Generally speaking, in an initial state such as during shipment and storage, packaging cover or cover 18 may be adapted to apply external pressure to the hub 30 and/or the shield 70 to prevent the drive member 80 from biasing the hub 30 and the shield 70 axially away from each other. Generally during use, a user grasps needle assembly 12 to apply external pressure to the hub 30 and/or the shield 70 and removes the packaging cover 18, with the user maintaining the external pressure on the hub 30 and/or the shield 70 until activation of the needle assembly 12 is desired. In this manner, needle assembly 12 represents a passively activatable structure in that activation occurs during the normal use of the needle assembly 12.

The hub 30 and safety shield 70 may be provided in various arrangements, as will now be discussed in more detail with reference to specific embodiments of the invention.

FIGS. 2-8 depict a specific embodiment of the invention in which the shield 70 is retained within the hub 30 against the bias of drive member 80. In particular, as shown in FIGS. 2-8, the hub 30 may include two opposing release members 44. The release members 44 generally extend along opposing sides 46, 48 of the hub 30 and form part of the body of the hub 30. The release members 44 are generally adapted to maintain the safety shield 70 and drive member 80 in a pre-actuated state or position within the body of the hub 30, and also operate to release or actuate the drive member 80, which is generally operable to move the safety shield 70 to a shielding position relative to the needle cannula 20, as discussed in detail herein.

The release members 44 are desirably pivotally connected to the hub 30, for example, by respective hinge structures 50 (i.e., hinges). The release members 44 are preferably integrally-molded with the body of the hub 30, which is preferably formed of molded plastic material. The hinge structures 50 are thus formed integrally (i.e., as a living hinge) with the release members 44 and the body of the hub 30. The hinge structures 50 permit the release members 44 to pivot relative to the body of the hub 30 and, in particular, to pivot inward toward a central longitudinal axis L of the blood collection set 10 and shielding needle assembly 12. Alternatively, the release members 44 may be formed separately from the hub 30 and connected thereto by conventional hinges. The release members 44 produce an angle vertex opening towards the distal end 34 of the hub 30. The release members 44 partially form the sidewall of the hub 30, but may pivotally extend inward into the hub 30.

The opposing release members 44 further include respective finger tabs 52 which provide locations for a user's fingers when manipulating the blood collection set 10 and needle assembly 12. The finger tabs 52 may include raised structures or protrusions 54, such as bumps, for improving the handling characteristics of the needle assembly 12 when manipulated by the user. The release members 44 each include distal ends 56 formed with opposing locking tabs 58, 60. The locking tabs 58, 60 are generally formed as inward-projecting locking tabs 58 and outward-projecting locking tabs 60, which are also referred to herein as first and second locking tabs 58, 60. The first or inward-projecting locking tabs 58 on the release members 44 are generally adapted to engage the safety shield 70, and the second or outward-projecting locking tabs 60 are generally adapted to engage the packaging cover 18, as discussed further herein.

In particular, in the embodiment of FIGS. 2-8, the safety shield 70 extends generally coaxially about needle cannula 20 and is movable along needle cannula 20 between a first or retracted position coaxially received within the hub 30 (See FIGS. 2-5), and a second or extended position (See FIGS. 6 and 7) generally encompassing the needle cannula 20 and, more particularly, the puncture tip 28. The drive member 80 is generally adapted to move the safety shield 70 axially along the needle cannula 20 from the retracted position to the extended position. In particular, the distal end 84 of the drive member 80 is generally in contact with the distal end 74 of the safety shield 70 and, in particular, an internal side 86 of the distal end 74 of the safety shield 70. The engagement of the distal end 84 of the drive member 80 with the distal end 74 of the safety shield 70 forms the physical interface between the drive member 80 and the safety shield 70 for moving the safety shield 70 from the retracted position to the extended position. The distal end 74 of the safety shield 70 further includes an outward-facing or distal end surface 88, which engages the first or inward-projection locking tabs 58 in the retracted position of the safety shield 70.

Alternatively, the release members 44 may represent the sidewalls of the hub 30, while they are radially flexible inwardly due to the physical structure of the hub 30. For example, the release members 44 (i.e., hub sidewalls) may be constructed to flex radially inwardly when external lateral pressure is applied to opposing sides of the hub 30. To facilitate this flexing, the opposing sidewalls of the hub 30 may be constructed or molded with a thinner thickness than the proximal or distal portions of the hub 30, allowing for flexing of the opposing sides of the hub 30 at the release members 44. Such inward radial pressure at the release members 44 creates a compressive force establishing a frictional engagement against the safety shield 70 to hold the safety shield 70 in the retracted position. Such an arrangement may also include the locking tabs 58, 60 for further retention of the safety shield 70.

The packaging cover 18 is provided on the distal end 34 of the hub 30 and is preferably secured to the hub 30 during manufacturing and assembly of the needle assembly 12. The packaging cover 18 is preferably in frictional engagement with the distal end 34 of the hub 30, and is generally adapted to maintain the needle assembly 12 in the pre-actuated state or condition shown, for example, in FIGS. 2-4, with the safety shield 70 in the retracted position. For this purpose, the packaging cover 18 may be formed with an internal locking groove 90, which is engaged by the second or outward-projecting locking tabs 60 formed at the distal ends 56 of the release members 44. The engagement of the outward-projecting locking tabs 60 secures the packaging cover 18 on the distal end 34 of the hub 30, with the aid of the drive member 80, until the needle assembly 12 is actuated by a user.

In the pre-actuated or "pre-packaged" state or condition of the needle assembly 12, the drive member 80 exerts a distally-directed force on the internal side 86 of the safety shield 70, which urges the distal end 74 of the safety shield 70 into engagement or contact with the first or inward-projecting locking tabs 58 formed on the distal ends 56 of the release members 44. In particular, the distal end surface 88 of the safety shield 70 is urged into contact or engagement with the first or inward-projecting locking tabs 58 on the distal ends 56 of the release members 44. Without the presence of the packaging cover 18, the distally-directed force acting on the distal ends 56 of the release members 44 would cause the release members 44 to pivot outward about their respective hinge structures 50. However, this distally-directed force is prevented from prematurely actuating the needle assembly 12 by the presence of the packaging cover 18, which provides a counter-acting radial force maintaining the compression of the drive member 80 within the safety shield 70 and hub 30. The engagement of the first or outward-projecting locking tabs 60 with the locking groove 90 in the packaging cover 18 prevents premature removal of the packaging cover 18 from the distal end 34 of the hub 30, and therefore premature actuation of the needle assembly 12.

An optional mechanism for retaining the packaging cover 18 onto hub 30 includes using the locking tabs 60 as external threads to ride within corresponding internal threads (not shown) in the packaging cover 18. In this embodiment, the internal threads would act more like slots than true threads, and the packaging cover 18 would have to be rotated to a position where the locking tabs 60 (i.e., external threads) would allow for the packaging cover 18 to be removed from the hub 30. An alternative configuration to the foregoing could include the locking tabs 60 engaging internal circumferential slots in the packaging cover 18 which connect to internal axial slots in the packaging cover 18. In such a variation, rotation of the packaging cover 18 would cause the locking tabs 60 to slide within the circumferential slots until reaching the axial slots, which would allow the packaging cover 18 to be removed from the hub 30.

The blood collection set 10 may be packaged in a conventional blister package (not shown). Prior to use, the blood collection set 10 is removed from its package and, if necessary, the second end 16 of the flexible tube 14 may be connected to an appropriate receptacle for providing fluid communication with the lumen 28 through the needle cannula 20. In use, the blood collection set 10 is provided with the needle assembly 12 and flexible tube 14 extending from needle assembly 12 and connected to an appropriate device (not shown), such as a blood collection receptacle.

Figure 4:
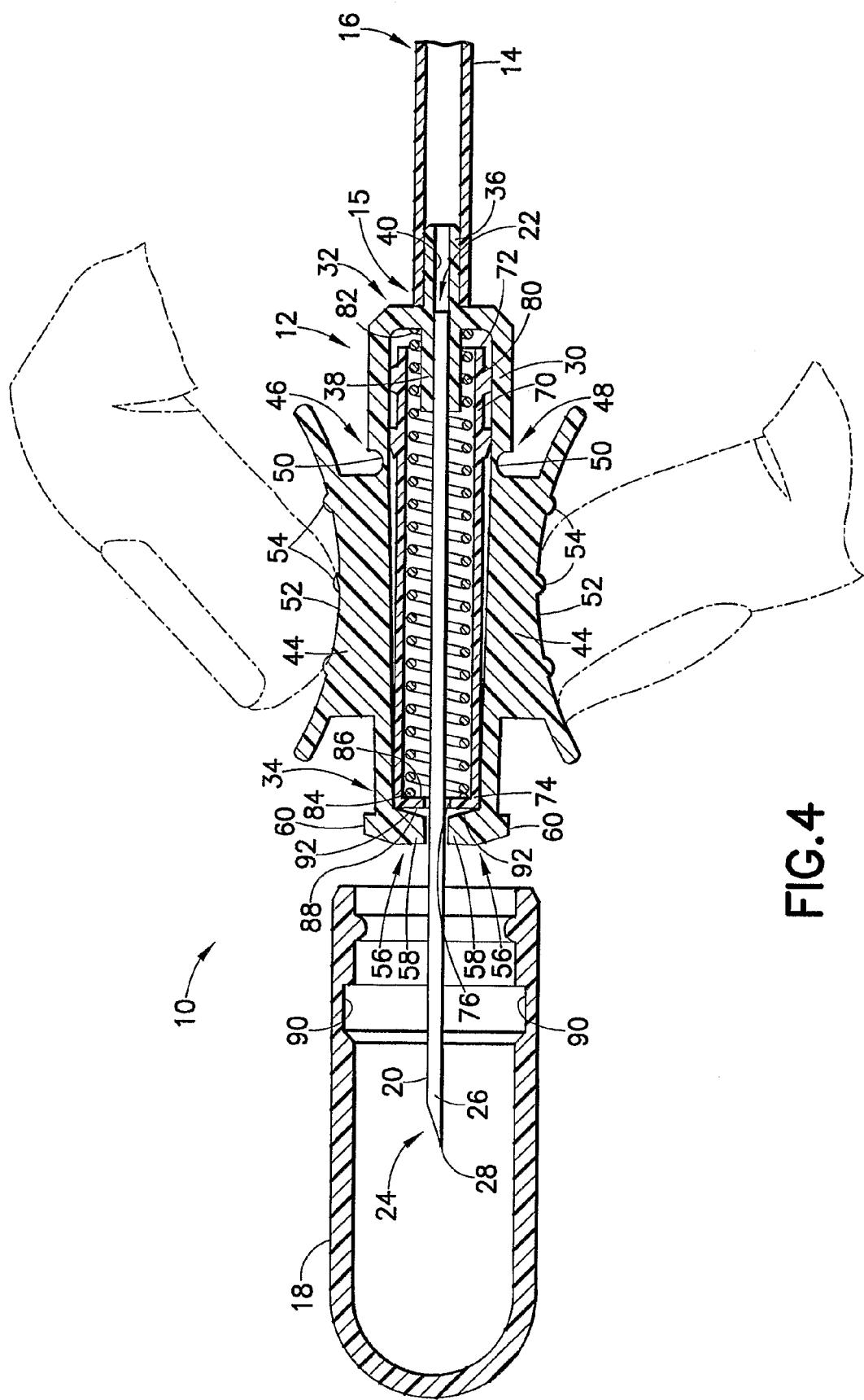
FIG. 4 is a longitudinal cross-sectional view of the needle device shown in FIG. 1, showing the user applying radial pressure to the needle device and the subsequent removal of the packaging cover.
Figure 5:
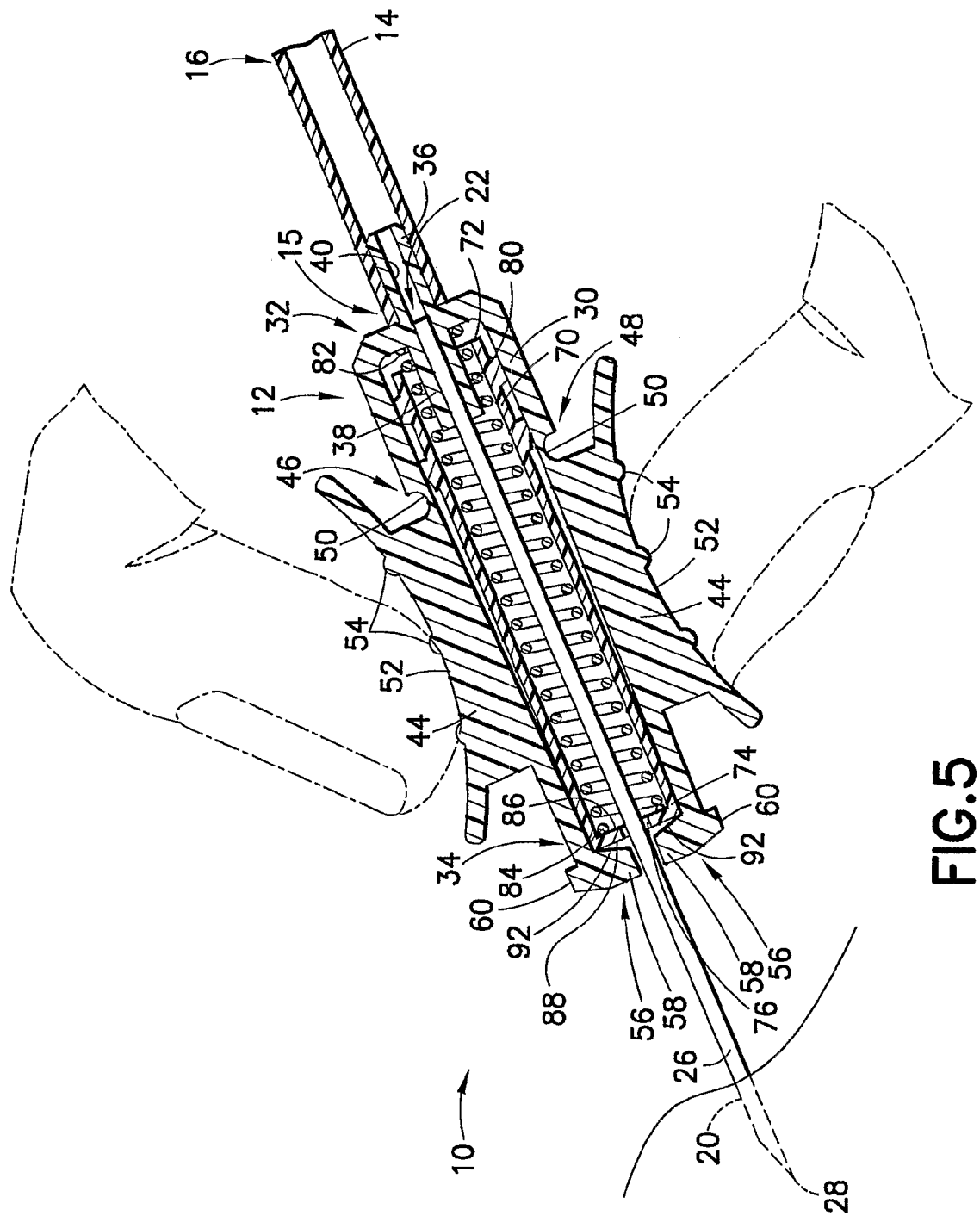
FIG. 5 is a cross-sectional view of the needle device shown in FIG. 1, showing a needle cannula inserted into the body of a patient.
Figure 8:
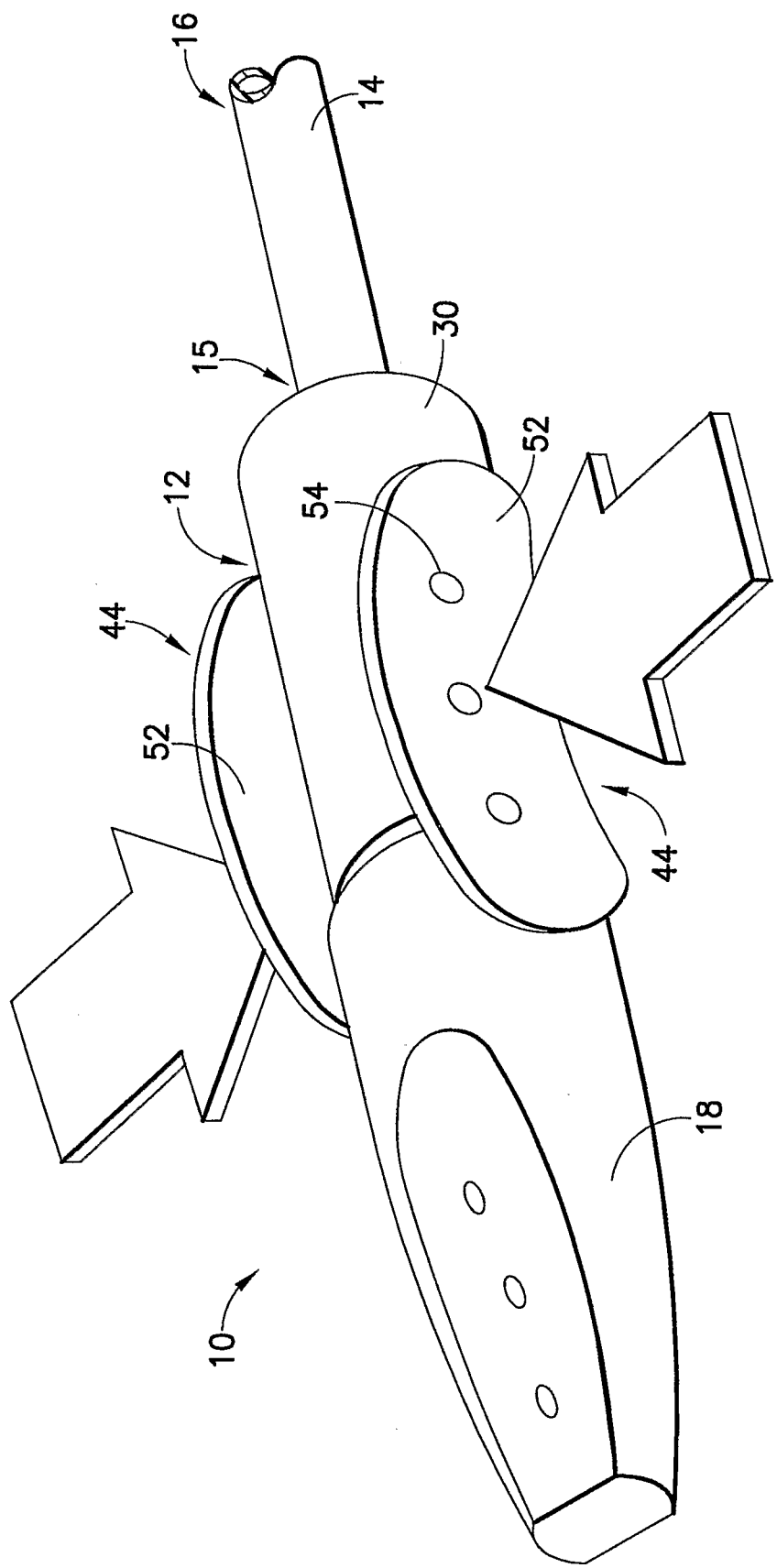
FIG. 8 is a perspective view showing the direction of forces for actuation of the shielding needle device.
Figure 9:
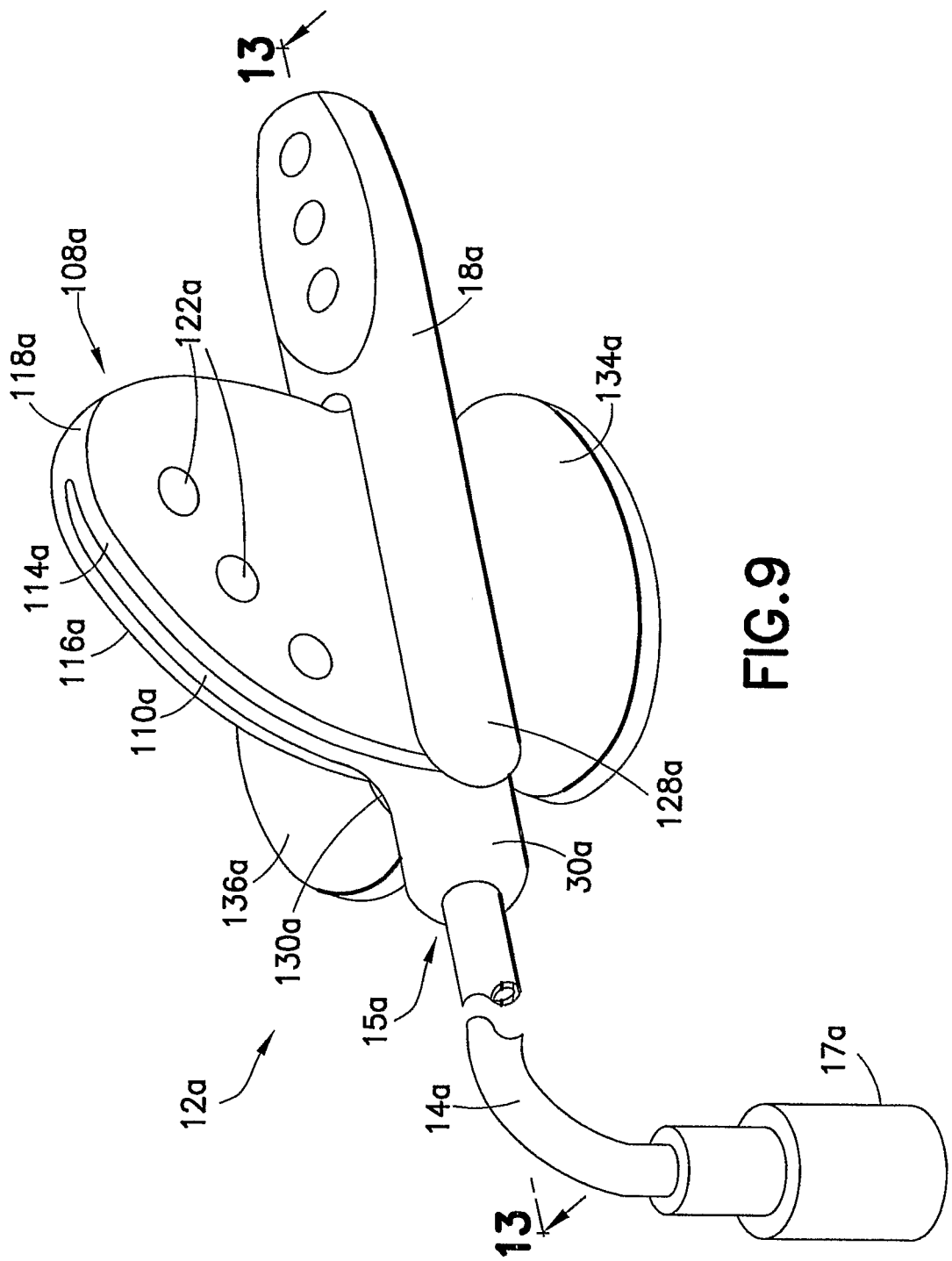
FIG. 9 is a perspective view of a shielding blood collection set including a needle device in accordance with another embodiment of the present invention, having a releasable packaging cover disposed at a distal end of the needle device.
Figure 10:
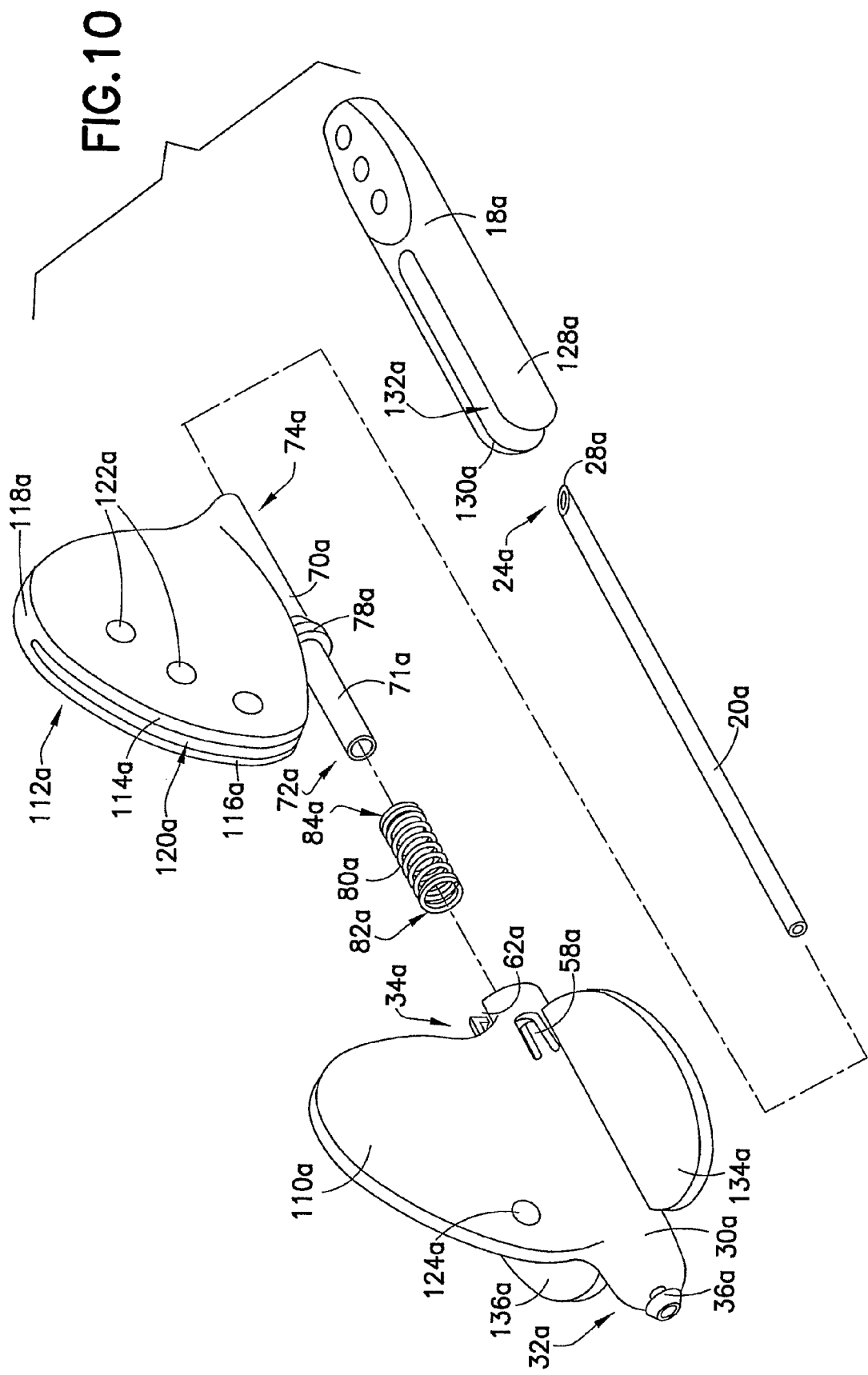
FIG. 10 is an exploded perspective view of the specific elements of the needle device shown in FIG. 9.

To use the blood collection set 10 and needle assembly 12, the user generally grasps the opposing finger tabs 52 provided on the needle assembly 12, as shown in FIGS. 3-5. The user then applies radial pressure to the finger tabs 52. FIG. 8 illustrates the direction of radially applied pressure that is necessary to begin actuation of the blood collection set 10 and needle assembly 12. As the user applies radial pressure to the finger tabs 52, the release members 44 will generally pivot inward toward the central longitudinal axis L of the blood collection set 10 and needle assembly 12. The release members 44 will generally pivot about their respective hinge structures 50, and will displace inward toward the central longitudinal axis L of the blood collection set 10 and needle assembly 12, as shown in FIG. 4. As shown in FIG. 4, the radial inward displacement of the release members 44 causes the second or outward-projection locking tabs 60 formed at the distal end 56 of the release members 44 to disengage substantially automatically from the locking groove 90 in the packaging cover 18. With the disengagement of the locking tabs 60 from the locking groove 90, the packaging cover 18 is releasable from secured engagement with the hub 30, and may be removed from the distal end 34 of the hub 30 by the user. The inward movement of the release members 44 generally reduces the diameter (i.e., cross-sectional area) of the distal end 34 of the hub 30 and automatically releases the packaging cover 18 from the distal end 34.

The user preferably maintains the radial force applied to the finger tabs 52, which causes the release members 44 to remain in substantially laterally-extending positions along the lateral sides 46, 48 of the hub 30. In this configuration, the first or inward-projection locking tabs 58 remain engaged with the outward-facing or distal end surface 88 at the distal end 74 of the safety shield 70, and prevents the drive member 80 from moving the safety shield 70 from the retracted position to the extended position. In particular, the distal end surface 88 of the safety shield 70 engages opposing inward-facing surfaces 92 on the first or inward-projection locking tabs 58 formed on the release members 44. The radial pressure applied by the user maintains the engagement of the locking tabs 58 with the distal end 74 of the safety shield 70, thereby maintaining the safety shield 70 in the retracted position and counteracting the distally-directed biasing force of the drive member 80. The radial pressure applied to the finger tabs 52 generally takes the place of the removed packaging cover 18 for maintaining the safety shield 70 in the retracted position and counteracting the biasing force of the drive member 80.

The user may then urge the puncture tip 28 at distal end 24 of the needle cannula 20 into a targeted blood vessel of a patient in order to conduct a blood collection procedure or other procedure as desired. When the user releases the radial pressure applied to the finger tabs 52, the drive member 80 is free to exert a distally-directed biasing force on the distal end 74 of the safety shield 70. In particular, with the release of the radial pressure, the drive member 80 urges the outward-facing or distal end surface 88 of the safety shield 70 to slide along the inward-facing surfaces 92 on the inward-projecting locking tabs 58, and generally urges the release members 44 to spread radially apart. The inward-facing surfaces 92 of the locking tabs 58 may be tapered to facilitate the sliding movement of the distal end surface 88 of the safety shield 70, and the concurrent outward-directed movement of the release members 44. As used in this disclosure, the term "release of radial pressure" and like phrases used to describe how the user actuates the needle assembly 12 is not intended to be limited to the complete discontinuing of radial pressure. This terminology is specifically intended to include such a complete discontinuing of radial pressure, such as the user totally removing his or her fingers from the finger tabs 52, as well as a partial or sequential lessening or reducing of radial pressure on the finger tabs 52 sufficient to allow the drive member 80 to move the locking tabs 58 out of engagement with the distal end 74 of the safety shield 70 and move the safety shield 70 to the extended or shielding position. The biasing force inherent in the drive member 80 as well as the profile of any interfering surfaces between the hub 30 and the shield 70 will determine the amount of lessening of the radial pressure required to allow the needle assembly 12 to actuate.

Figure 6:
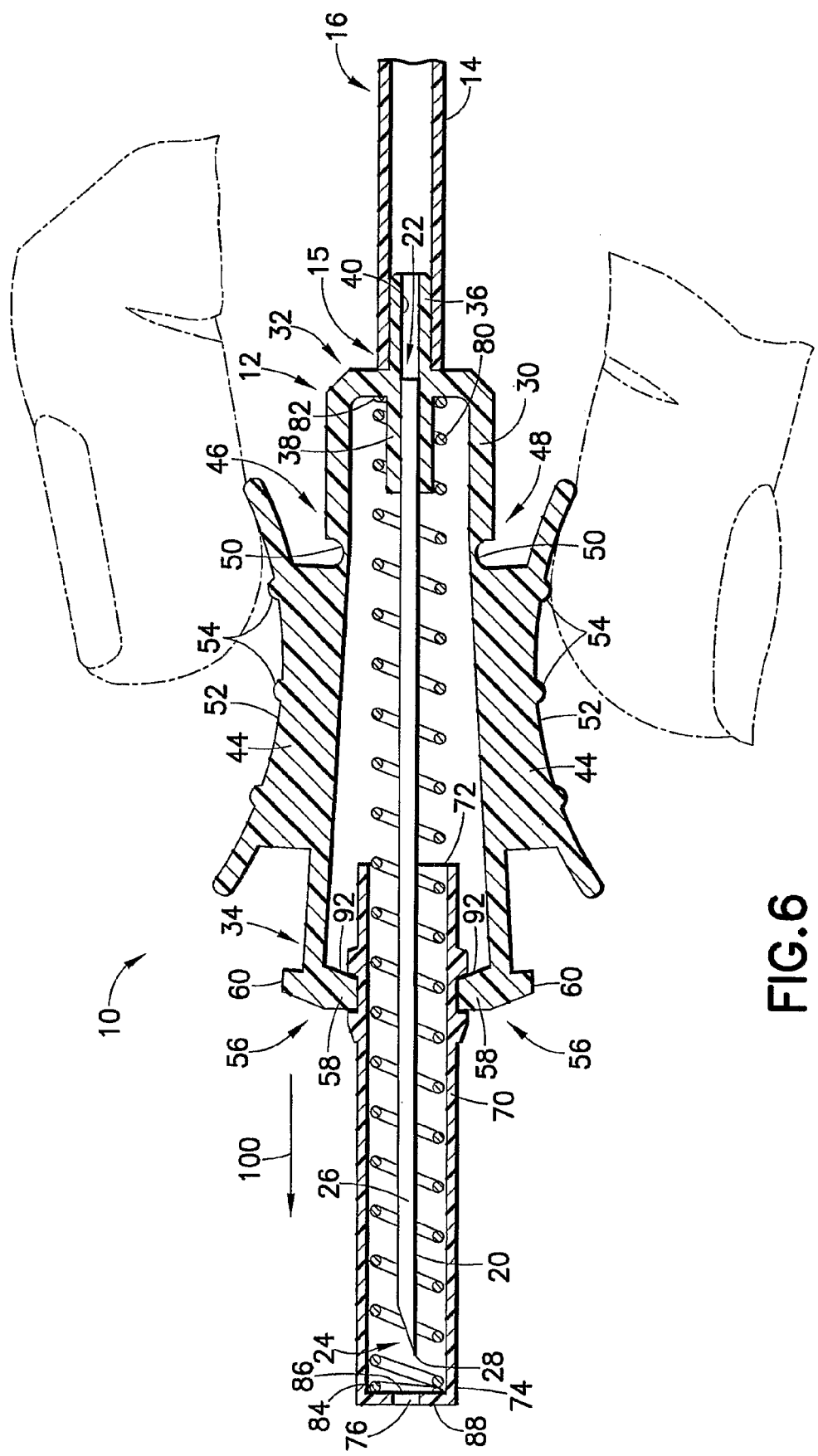
FIG. 6 is a longitudinal cross-sectional view of the needle device shown in FIG. 1, showing the needle device after the user has substantially released the radial pressure allowing shielding of the needle cannula.
Figure 7:
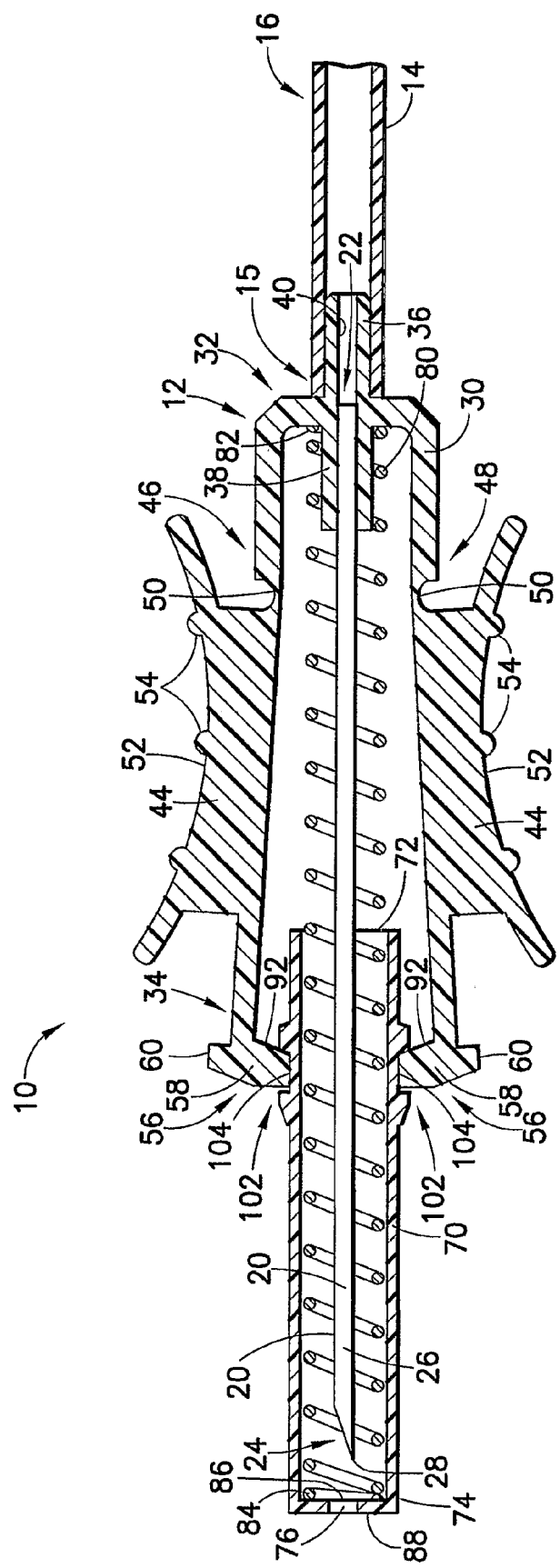
FIG. 7 is a longitudinal cross-sectional view of the needle device shown in FIG. 1, showing the final disposition with shielding of the needle cannula.

Once the locking tabs 58 are displaced radially out of engagement with the distal end 74 of the safety shield 70, the safety shield 70 is completely unrestrained and subject entirely to the distally-directed biasing force of the drive member 80. The drive member 80 propels the safety shield 70 distally along needle cannula 20 in an axial direction of arrow 100 (see FIG. 6), with the safety shield 70 sliding or gliding along needle cannula 20 toward distal end 24. During an actual blood collection procedure, the distal movement of the safety shield 70 will terminate when the distal end 74 of the safety shield 70 contacts the skin of the patient, as shown in FIG. 5. The drive member 80 still exerts a distally-directed biasing force on the safety shield 70, but this force is resolved by the frictional force that acts on the needle cannula 20, as a result of being in the blood vessel of the patient. The user may then proceed to complete the blood collection procedure, for example, using evacuated blood collection tubes or a syringe. The user then proceeds to remove the blood collection set 10 from the blood vessel of the patient using the finger tabs 52. As the needle cannula 20 is removed from the blood vessel of the patient, the safety shield 70 is urged by the drive member 80 to move closer to the distal end 24 of the needle cannula 20. As the needle cannula 20 is fully removed from the patient's blood vessel, the safety shield 70 is urged by the drive member 80 to fully encompass the needle cannula 20, as generally depicted in FIGS. 6 and 7. The drive member 80 now extends internally between the distal end 74 of the safety shield 70 and the internal structure 38 formed within the hub 30 at the proximal end 32 of the hub 30, and exerts a biasing force that will aid in preventing the re-emergence of the puncture tip 28 from the central opening 76 in the distal end 74 of the safety shield 70.

The safety shield 70 may further includes an external locking structure 102 for securing the safety shield 70 in the extended position, once the needle assembly 12 has been actuated. The external locking structure 102 may incorporate an external locking recess or groove 104, which is configured to be engaged by the inward-projecting locking tabs 58 when the safety shield 70 is moved to the extended position. In particular, when the safety shield 70 is moved to the extended position by the drive member 80, the locking tabs 58 preferably snap into engagement with the locking recess 104. It will be appreciated that the external locking recess 104 need not be continuous about the circumference of the safety shield 70. Likewise, the internal locking groove 90 in the packaging cover 18 need not be continuous around the internal circumference of the packaging cover 18. Moreover, it will further be appreciated that the needle assembly 12 may be configured to operate with a single release member 44 rather than the opposing pair of release members 44 discussed previously. However, the use of two opposing release members 44 is believed to be more intuitive for the user of the blood collection set 10 and needle assembly 12, and is presently preferred.

An alternate version of the above-described needle assembly is depicted in a further embodiment described with particular reference to FIGS. 9-19. The embodiment of FIGS. 9-19 generally depicts a specific embodiment of the invention in which the shield is retained within the hub against the bias of drive member through a dorsal grasping structure, with a dorsal member and dorsal gripping structure adapted for providing engagement between the hub and the shield upon application of external pressure thereto to retain the shield with respect to the hub against the bias of the drive member. In the embodiment described with reference to FIGS. 9-19, similar components performing similar functions will be numbered identically to those components of FIGS. 1-8, except that a suffix "a" will be used to identify those similar components in FIGS. 9-19.

Needle assembly 12*a* as shown in FIGS. 9-19 includes a housing in the form of hub 30*a* similar to that described above in connection with FIGS. 1-8, with a rearward or proximal end 32*a* and a forward or distal end 34*a*, and including an external structure 36*a* for mating with the first end 15*a* of the flexible tube 14*a*, and an internal structure 38*a* for engaging the drive member 80*a* and for supporting needle cannula 20*a*. The second end 16*a* of the flexible tube 15*a* may also include a fixture 17*a* for connection with a separate medical device, for example, to provide a blood collection set 10*a*. The proximal end 22*a* of needle cannula 20*a* is supported at internal structure 38*a*, and extends through the internal passageway 42*a* of hub 30*a*, with puncture tip 28*a* extending out from the distal end 34*a* thereof.

Figure 11:
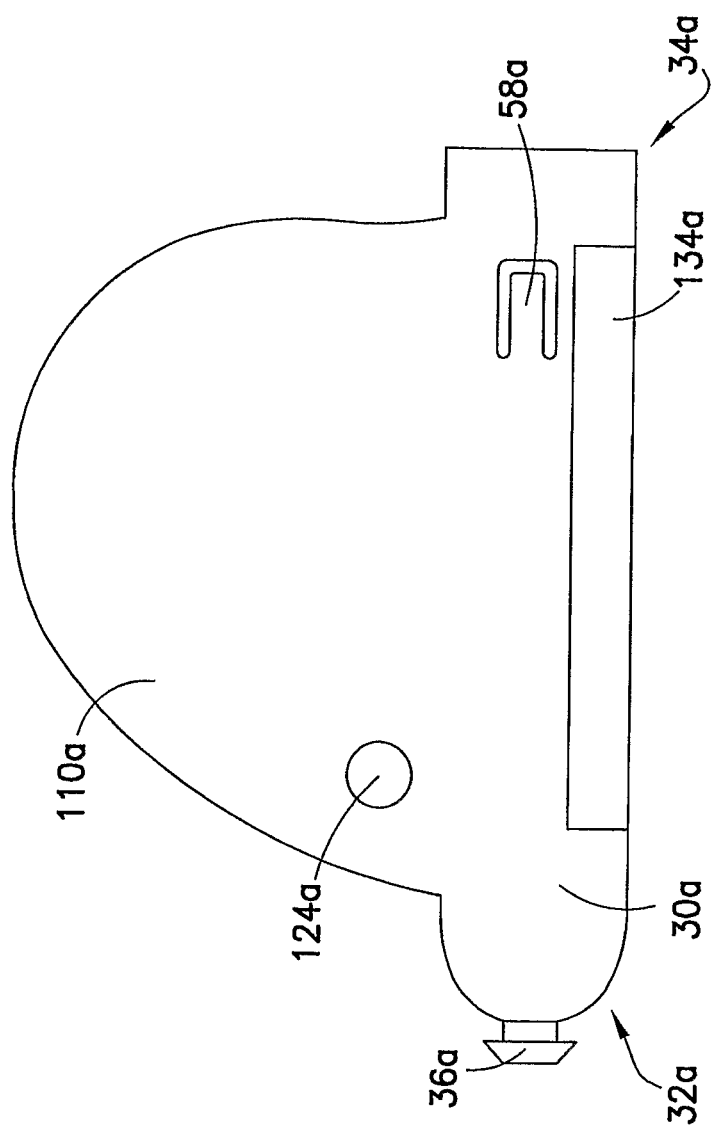
FIG. 11 is a side view of the hub of the needle device of FIG. 9.
Figure 15:
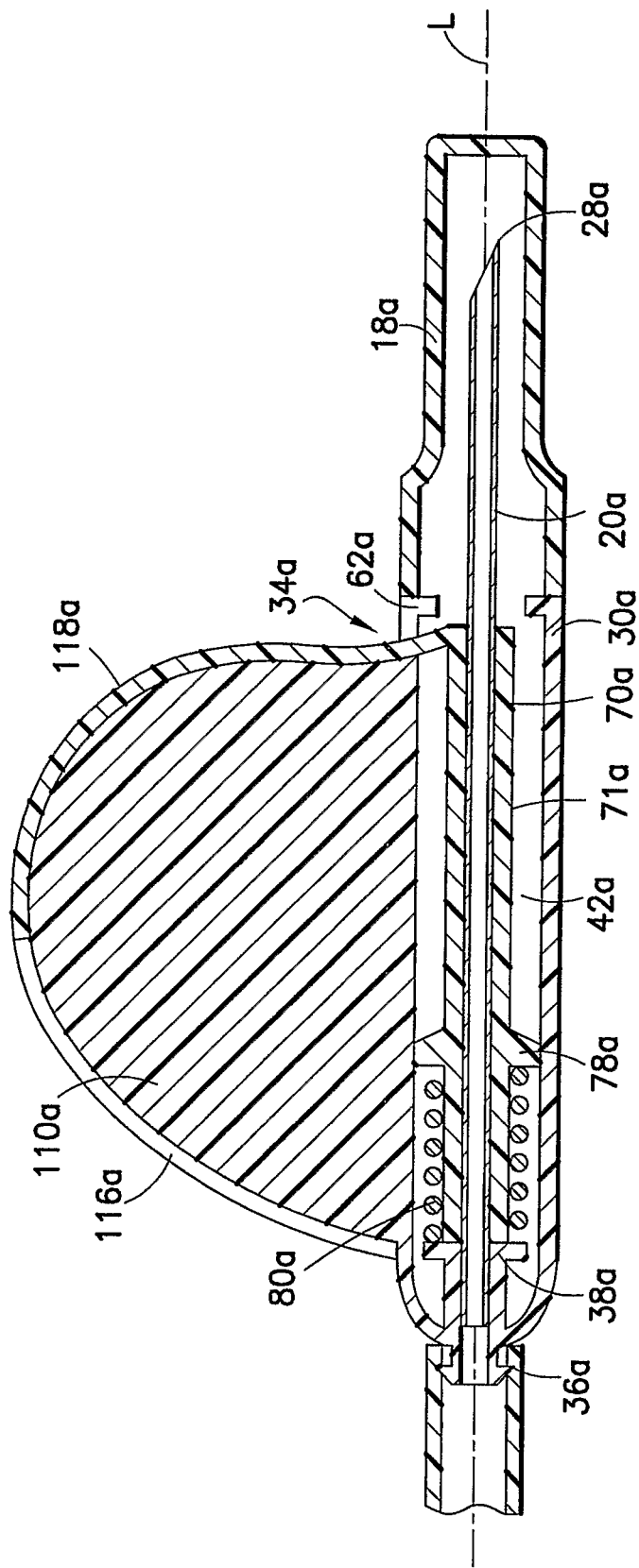
FIG. 15 is a longitudinal cross-sectional view of the needle device taken along lines 15-15 of FIG. 9.
Figure 16:
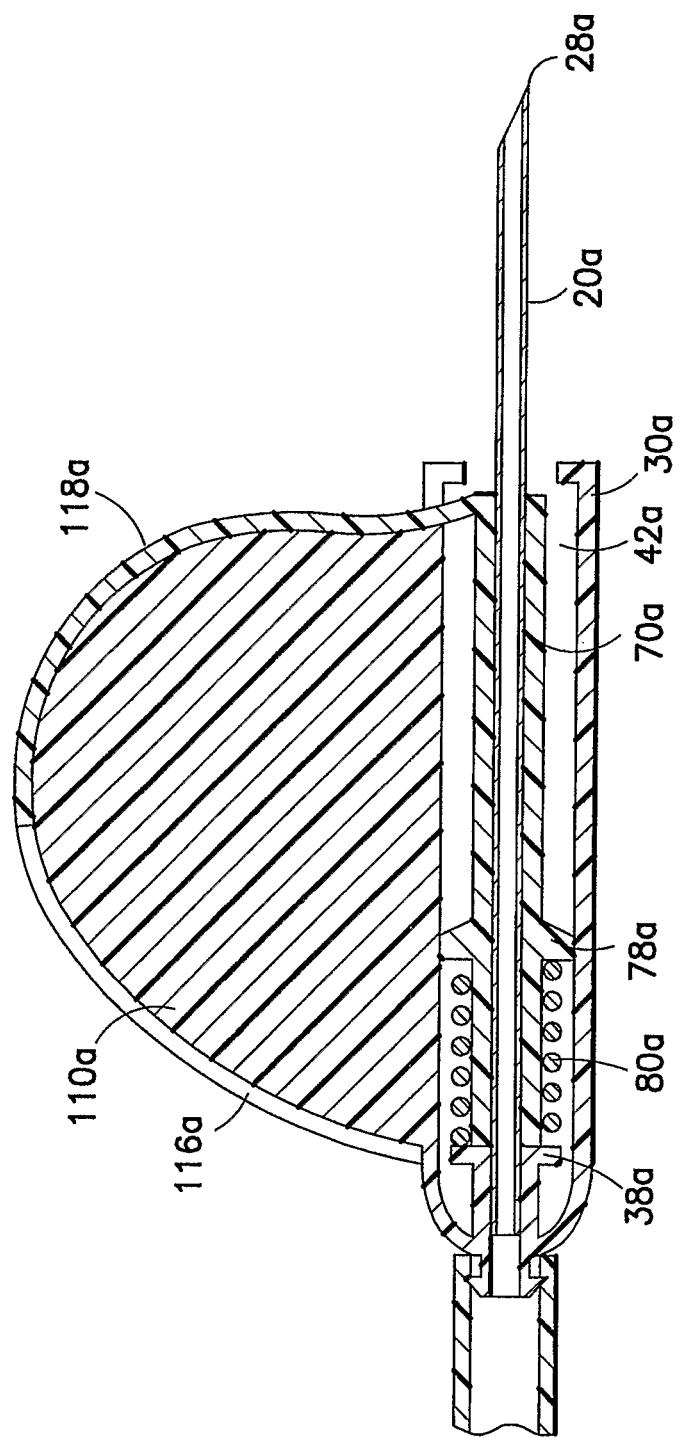
FIG. 16 is a longitudinal cross-sectional view of the needle device taken along lines 16-16 of FIG. 13.
Figure 17:
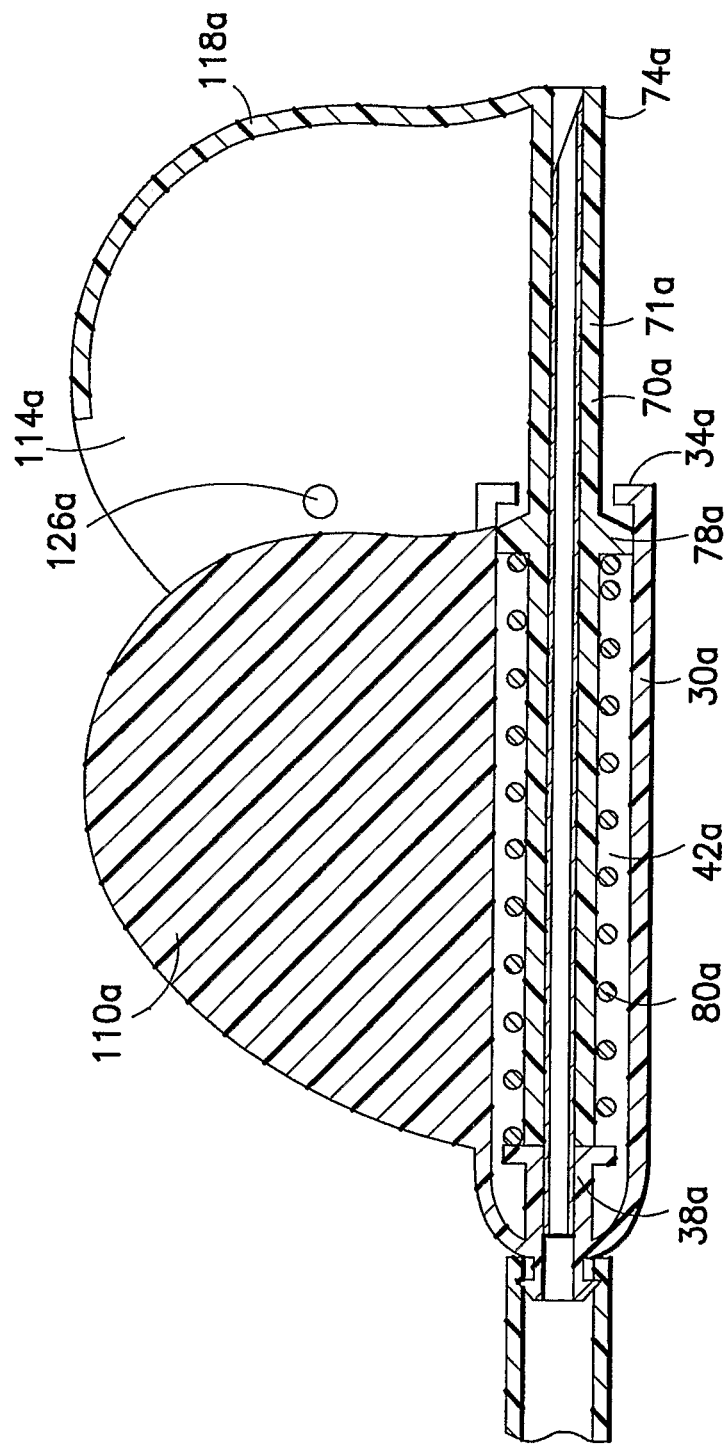
FIG. 17 is a longitudinal cross-sectional view of the needle device taken along lines 17-17 of FIG. 14.

Shield 70*a* extends generally coaxially about needle cannula 20*a* and is movable along needle cannula 20*a* between a first or retracted position coaxially received within the passageway 42*a* of hub 30*a* as shown in FIGS. 11 and 15, and a second or extended position generally encompassing the needle cannula 20*a* and, more particularly, the puncture tip 28*a* as shown in FIGS. 16 and 17. The drive member 80*a* is generally adapted to move the shield 70*a* axially along the needle cannula 20*a* from the retracted position to the extended position. In particular, the distal end 84*a* of the drive member 80*a* is generally in contact with a portion of the shield 70*a* such as an abutment structure 78*a* provided on an external surface of the shield 70*a*. The engagement of the distal end 84*a* of the drive member 80*a* with the abutment structure 78*a* of the shield 70*a* forms the physical interface between the drive member 80*a* and the shield 70*a* for moving the shield 70*a* from the retracted position to the extended position.

Needle assembly 12*a* includes structure adapted to maintain the shield 70*a* and drive member 80*a* in a pre-actuated state or position within the body of the hub 30*a* and to release or actuate the drive member 80*a*, in a similar manner as with release members 44 described above with reference to FIGS. 1-8. In particular, in the present embodiment, engagement between the hub 30*a* and the shield 70*a* is provided through an actuation mechanism in the form of a dorsal grasping structure 108*a* including a dorsal member 30*a* extending from an external surface of the hub 30*a* and a grip structure 112*a* extending from an external surface of the shield 70*a*. Dorsal grasping structure 108*a* is generally symmetrically aligned with the bevel-up orientation of the puncture tip 28*a* of the needle cannula 20*a*.

More particularly, hub 30*a* includes dorsal member 110*a*, which extends dorsally from a top surface thereof in the form of a generally planar spine member extending in a plane corresponding to longitudinal axis L defined by the needle cannula 20*a*. Shield 70*a* includes a main body portion such as tubular body 71*a*, with a grip structure 112*a* extending from the top surface of the body 71*a* of shield 70*a* at the forward or distal end 74*a* thereof. Grip structure 112*a* of shield 70*a* includes a profile generally corresponding to the dorsal member 110*a*, and may be in the form of at least one, and preferably a pair of flexibly resilient planar leafs 114*a*, 116*a*, uniting at forward ends thereof through a bridge 118*a*. In this manner, the grip structure 112*a* extends from the body 71*a* of shield 70*a* through the bridge 118*a*, with planar leafs 114*a*, 116*a* extending toward the rearward or proximal end 72*a* of the shield 70*a* along a top end of the body 71*a*. The planar leafs 114*a*, 116*a* are spaced from each other to define an opening or gap 120*a* therebetween for accommodating the spine of dorsal member 30*a* therein when the shield 70*a* is in the retracted position within hub 30*a*. The planar leafs 114*a*, 116*a* are resilient members which can be bent or flexed toward each other, and are therefore essentially pivotally connected through the bridge 118*a* in a hinged manner. The shield 70*a* is preferably molded as a single structure of molded plastic material including the body 71*a*, bridge 118*a* and planar leafs 114*a*, 116*a* integrally formed. Additionally, one or more bumps 122*a* may be provided on an external surface of one or both of planar leafs 114*a*, 116*a*, providing a tactile surface for the user to grasp the grip structure 112*a* during use.

Shield 70*a* extends coaxially within the internal passageway 42*a* of hub 30*a*. To assist in accommodating the grip structure 112*a* of shield 70*a* therein, hub 30*a* may include a cutaway portion 62*a* at a top surface adjacent distal end 34*a* thereof. In this manner, the bridge 118*a* of shield 70*a* can be slidably accommodated within cutaway portion 62a of hub 30a when the shield 70a is maintained in the first position retracted within the hub 30a.

External pressure applied between the grip structure 112a of the shield 70a and the dorsal member 110a of the hub 30a maintains the shield 70a in the retracted position against the bias of the drive member 80a. In particular, in the embodiment of FIGS. 9-19, external pressure applied between the planar leafs 114a, 116a, establishes frictional engagement between one or both of the planar leafs 114a, 116a and dorsal member 110a of hub 30a, thereby maintaining the shield 30a in fixed relation with respect to the hub 30a against the bias of the drive member 80a, as will be discussed in more detail herein. Such inward pressure at the planar leafs 114a, 116a creates a compressive force establishing a frictional engagement against the spine of dorsal member 110a, thereby holding the safety shield 70a in the retracted position with respect to the hub 30a. It is contemplated that the grip structure 112a may include only a single planar leaf extending from the shield 70a, in which case engagement of the single planar leaf with the dorsal member 110a of the hub 30a is accomplished by gripping directly between the single planar leaf and the dorsal member 110a between the user's fingers.

Moreover, the planar leafs 114a, 116a, and the dorsal member 110a may include corresponding structure adapted for interference engagement therebetween when external pressure is applied. For example, dorsal member 110a may include one or more detents 124a on an external surface thereof, and planar leafs 114a, 116a may include one or more corresponding protrusions or protuberances 126a on a corresponding surface within gap 120a. The opposing planar leafs 114a, 116a may also include structure on external finger surfaces thereof for providing a tactile feel for a user's fingers when manipulating the needle assembly 12a and during use, such as raised structures or protrusions in the form of bumps 122a.

Figure 12:
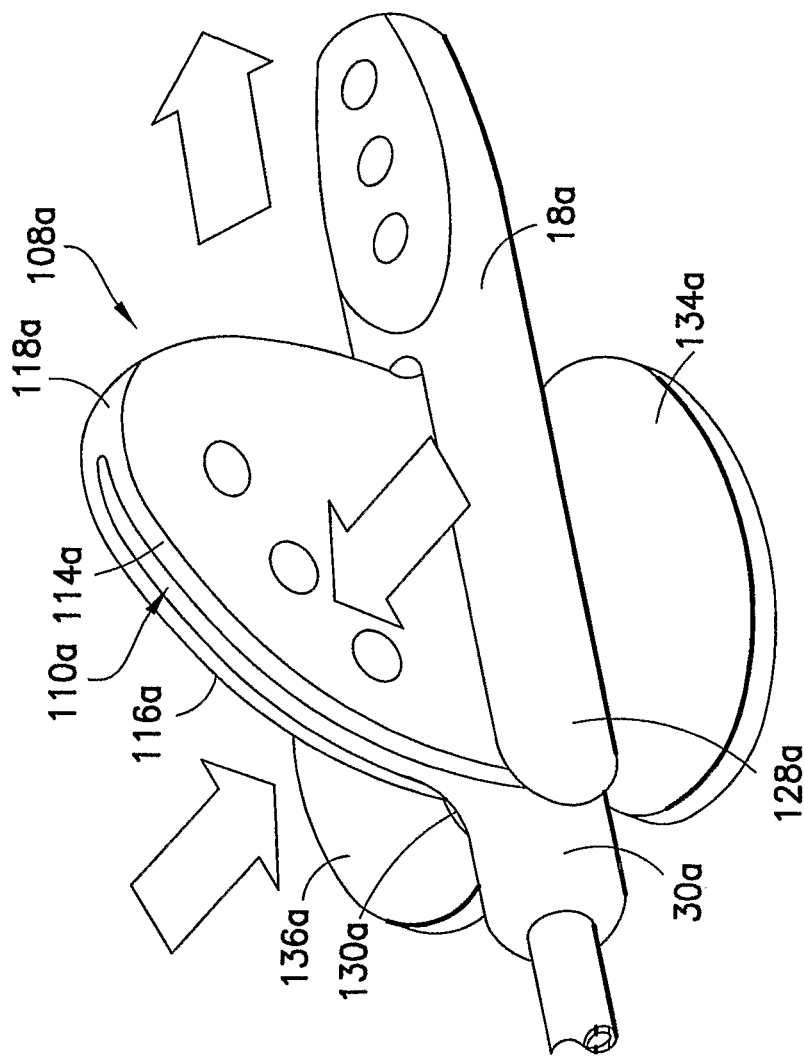
FIG. 12 is a perspective view showing the direction of forces for actuation of the shielding needle device of FIG. 9.
Figure 13:
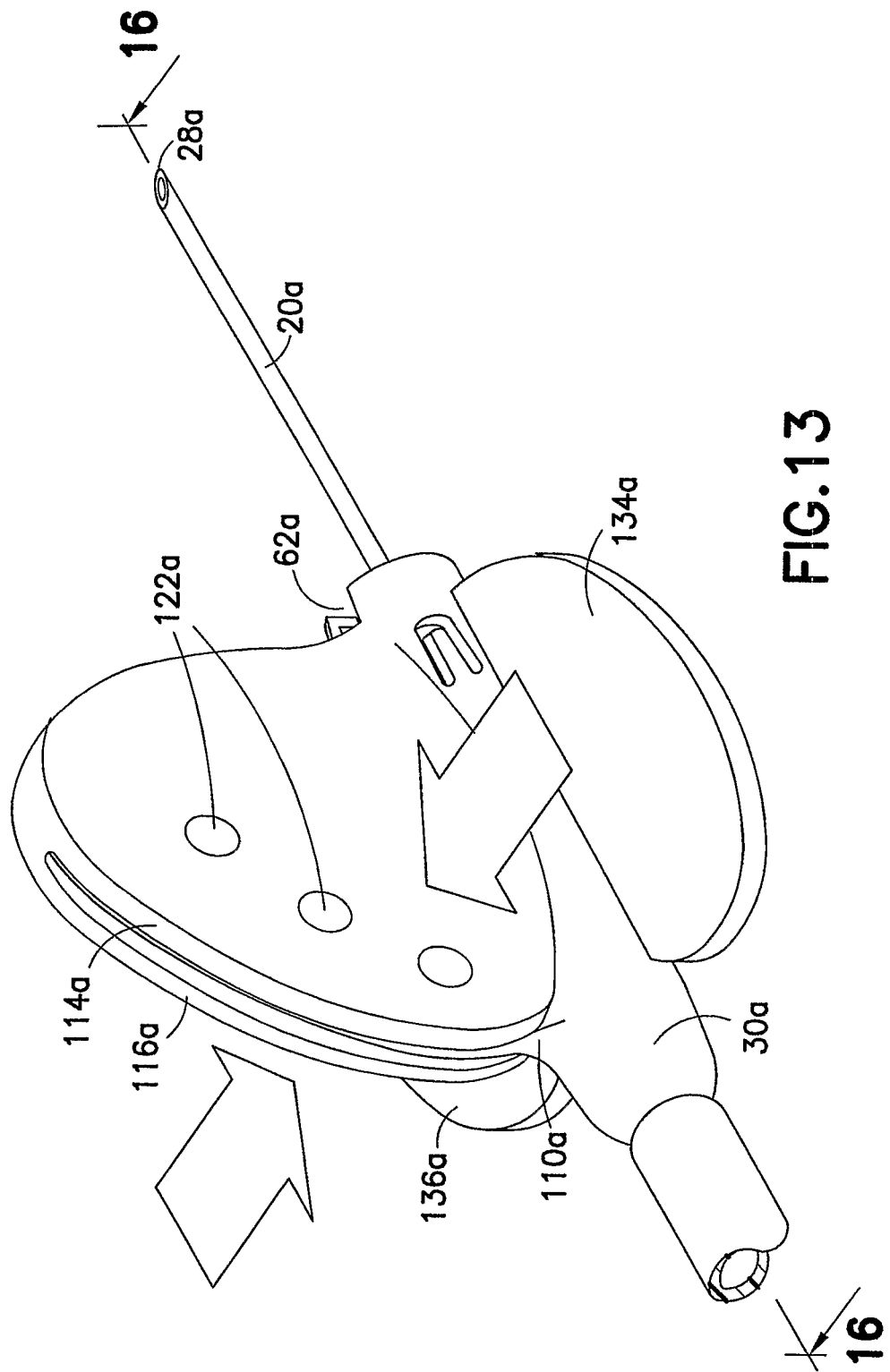
FIG. 13 is a perspective view showing of the shielding needle device of FIG. 9 with the packaging cover removed in the retracted position with the needle cannula exposed for use.

A packaging cover 18a may also be provided on the distal end 34a of the hub 30a in a similar manner as described above with respect to FIGS. 1-8. The packaging cover 18a is preferably in frictional engagement with the hub 30a, and is generally adapted to maintain the needle assembly 12a in the pre-actuated state with the safety shield 70a in the retracted position. In this manner, the packaging cover 18a includes opposing longitudinal arms 128a and 130a, with an opening 132a extending therebetween. With packaging cover 18a secured to the distal end 34a of hub 30a, longitudinal arms 128a and 130a extend rearward along opposing lateral sides of hub 30a. Longitudinal arms 128a and 130a are desirably constructed in a manner so as to be naturally biased radially inwardly, so as to exert a radially compressive force against the outer surface of hub 30a, thereby maintaining packaging cover 18a in a frictional fit over hub 30a. The packaging cover 18a may contact the distal end 74a of the shield 70a, with the radial compressive force of the longitudinal arms 128a and 130a being sufficiently strong so as to maintain shield 70a in the retracted position against the bias of drive member 80a. Moreover, the longitudinal arms 128a and 130a may be sized and shaped so as to contact at least a portion of the respective external surfaces of planar leafs 114a, 116a. In this manner, the radially compressive force exerted by the longitudinal arms 128a and 130a will be transferred to the planar leafs 114a, 116a, thereby providing an external compressive force thereagainst as depicted in FIG. 12 to further maintain shield 70a in the retracted position with respect to hub 30a. In addition or alternatively thereto, the packaging cover 18a may include structure for interlocking engagement with a portion of shield 70a as described above with reference to FIGS. 1-8, such that when planar leafs 114a, 116a are grasped during use, packaging cover 18a is released.

The hub 30a may further include a pair of wings 134a, 136a, extending laterally from opposing sides of the hub 30a. The wings 134a, 136a are fixed in relation to the hub 30a, and are desirably integrally molded with the hub 30a as a rigid structure. The wings 134a, 136a provide structure for guiding the needle assembly 12a during use thereof, and can be taped to the skin of a patient to maintain the needle assembly 12a in a fixed position during use in a medical procedure such as blood collection. Desirably, the dorsal grasping structure 108a formed by the engagement between the planar leafs 114a, 116a and dorsal member 110a has a profile larger than the profile of wings 134a, 136a. In this manner, a user is encouraged to grasp the needle assembly 12a by the dorsal grasping structure 108a for use, as opposed to grasping needle assembly 12a by attempting to bend wings 134a, 136a toward each other, as is common with conventional needle assemblies.

To use the needle assembly 12a of the embodiment set forth in FIGS. 9-19, the user generally grasps the dorsal grasping structure 108a to apply external pressure between opposing surfaces of the planar leafs 114a, 116a and the dorsal member 110a in the direction of shown in FIG. 15. As the user applies external pressure to the planar leafs 114a, 116a, the packaging cover 18a is removed from the distal end 34a of the hub 30a by the user. The user maintains the external force applied to the planar leafs 114a, 116a, which causes them to engage with the dorsal member 110a of the hub 30a in a frictional engagement, and in particular causes the protrusions 126a on the planar leafs 114a, 116a to engage the corresponding detents 124a on the dorsal member 110a in an interference engagement. In this manner, the pressure applied by the user maintains the engagement between the planar leafs 114a, 116a and the dorsal member 110a, thereby maintaining the safety shield 70a in the retracted position and counteracting the distally-directed biasing force of the drive member 80a. The radial pressure applied to the planar leafs 114a, 116a generally takes the place of the removed packaging cover 18a for maintaining the safety shield 70a in the retracted position and counteracting the biasing force of the drive member 80a.

Figure 14:
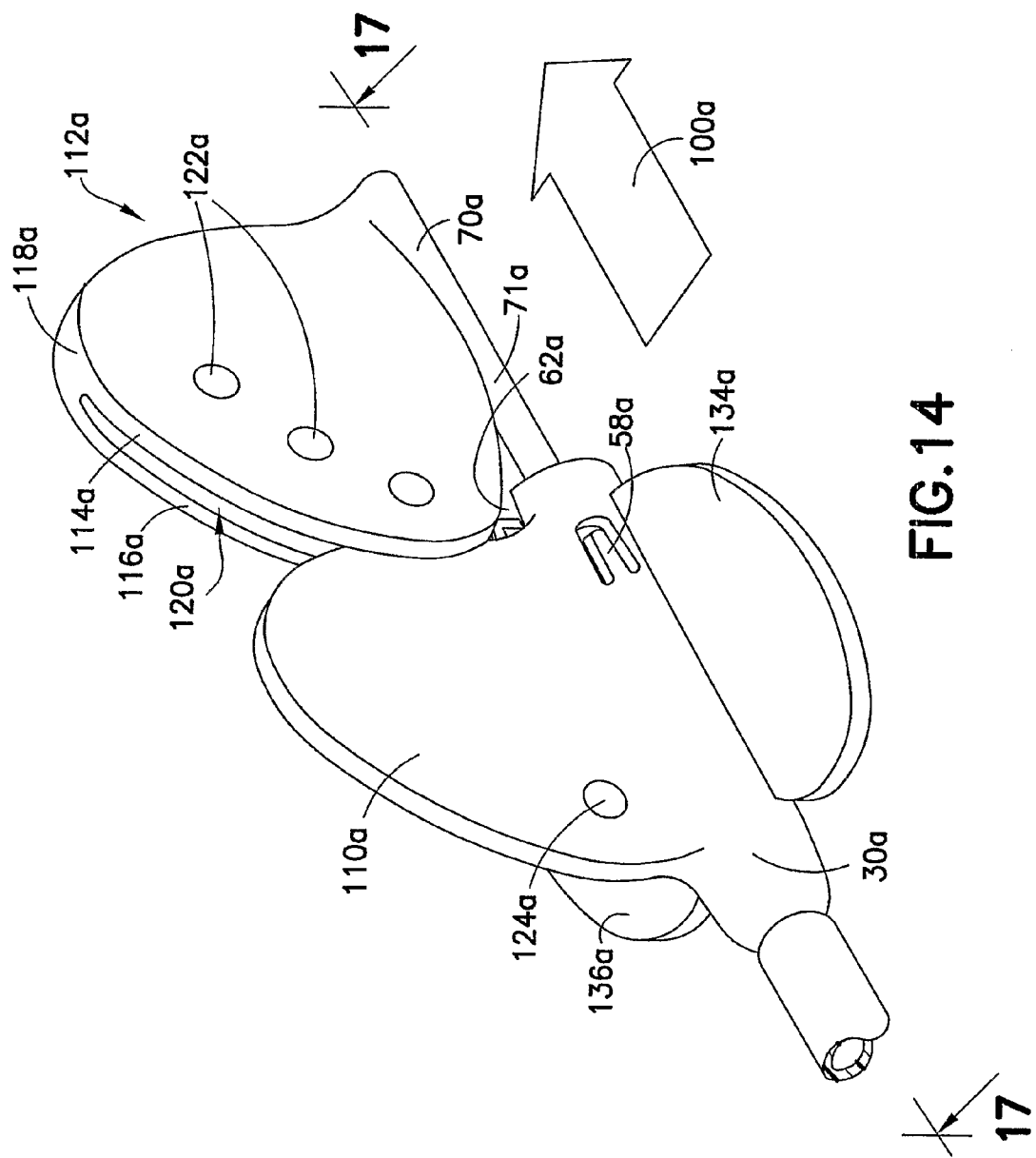
FIG. 14 is a perspective view showing of the shielding needle device of FIG. 9 in the extended position with the shield encompassing the needle cannula.

The user may then urge the puncture tip 28a at distal end 24a of the needle cannula 20a into a targeted blood vessel of a patient in order to conduct a blood collection procedure or other procedure as desired. After proper positioning, when the user releases the applied pressure applied to the planar leafs 114a, 116a, the drive member 80a is free to exert a distally-directed biasing force on the distal end 74a of the safety shield 70a. The drive member 80a then propels the safety shield 70a distally along needle cannula 20a in an axial direction of arrow 110a in FIG. 14, with the safety shield 70a sliding or gliding along needle cannula 20a toward distal end 24a. During an actual blood collection procedure, the distal movement of the safety shield 70a will terminate when the distal end 74a of the safety shield 70a contacts the skin of the patient. The drive member 80a still exerts a distally-directed biasing force on the safety shield 70a, but this force is resolved by the frictional force that acts on the needle cannula 20a, as a result of being in the blood vessel of the patient. The user may then proceed to complete the blood collection procedure, for example, using evacuated blood collection tubes or a syringe. The user then proceeds to remove the needle assembly 12a from the blood vessel of the patient by grasping the dorsal member 110a. As the needle cannula 20a is removed from the blood vessel of the patient, the safety shield 70a is urged by the drive member 80a to move closer to the distal end 24*a* of the needle cannula 20*a*. As the needle cannula 20*a* is fully removed from the patient's blood vessel, the safety shield 70*a* is urged by the drive member 80*a* to fully encompass the needle cannula 20*a*, as generally depicted in FIGS. 14 and 17. The drive member 80*a* exerts a biasing force that will aid in preventing the re-emergence of the puncture tip 28*a* from the central opening 76*a* in the distal end 74*a* of the safety shield 70*a*.

Figure 18:
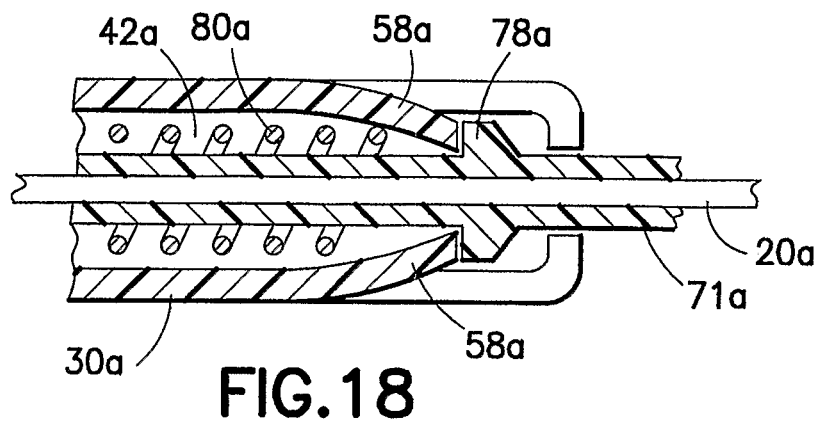
FIG. 18 is a partial cross-sectional view of the needle device in the extended position as shown in the FIG. 14, depicting the locking elements for maintaining the shield in the shielding position.
Figure 19:
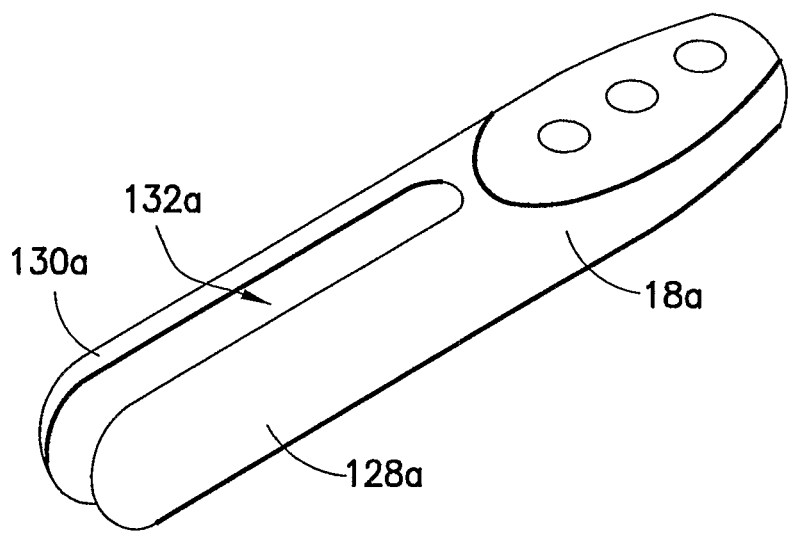
FIG. 19 is a perspective view of a packaging cover in accordance with the embodiment of FIG. 9.
Figure 20:
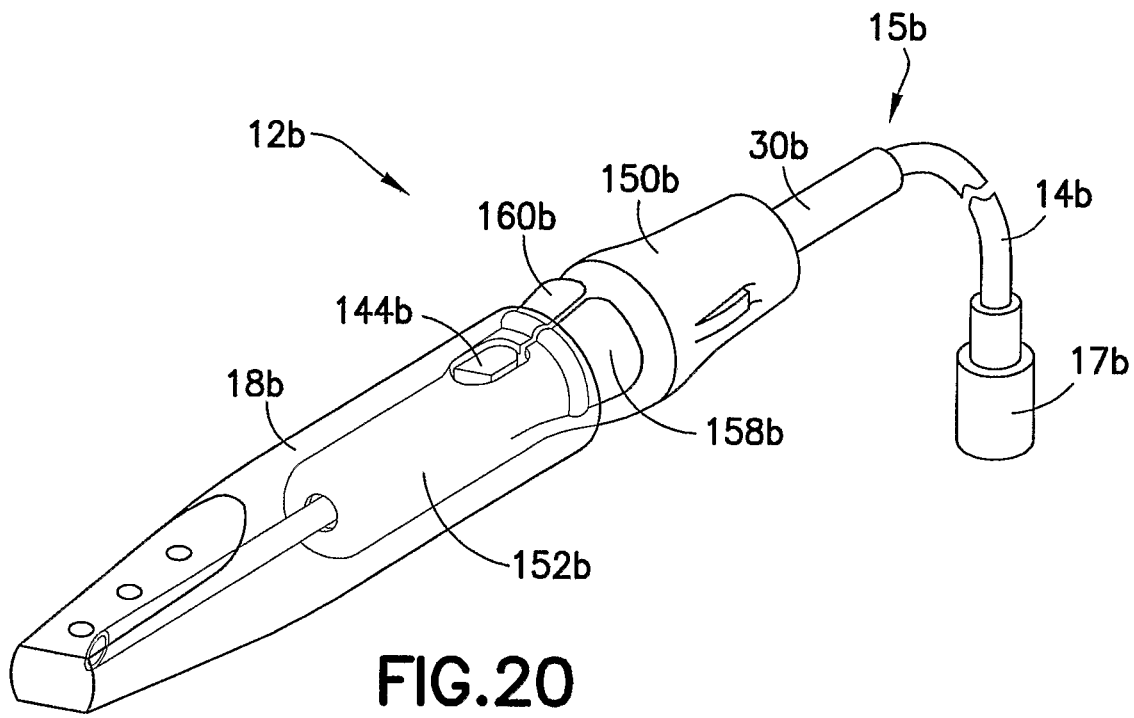
FIG. 20 is a perspective view of a shielding blood collection set including a needle device in accordance with a further embodiment of the present invention, having a releasable packaging cover disposed at a distal end of the needle device.

The safety shield 70*a* and the hub 30*a* may further include interengaging structure for interfering engagement therebetween for securing the safety shield 70*a* in the extended position to prevent a return movement once the needle assembly 12*a* has been actuated. For example, the safety shield 70*a* may include external locking structure in a similar manner as described above with respect to FIGS. 1-8, such as an external locking recess or groove, which is preferably provided through abutment structure 78*a* in the embodiment of FIGS. 9-19, and which is configured to be engaged by the inward-projecting locking tabs 58*a* on opposing lateral sides of hub 30*a* when the safety shield 70*a* is moved to the extended position, as shown in FIG. 18. Needle assembly 12*a* can thereafter be appropriately discarded.

A further variation of the needle assembly is depicted in yet a further embodiment described with particular reference to FIGS. 20-33. The embodiment of FIGS. 20-33 generally depicts a specific embodiment of the invention in which the shield is a barrel-like structure maintained coaxially about the hub against the bias of the drive member, with one or more corresponding release tabs of the shield adapted for providing engagement with a release member of the hub upon application of external pressure thereto to maintain the shield and the hub in fixed relation against the bias of the drive member. In the embodiment described with reference to FIGS. 20-33, similar components performing similar functions will be numbered identically to those components of FIGS. 1-8, except that a suffix "b" will be used to identify those similar components in FIGS. 20-33.

Figure 23A:
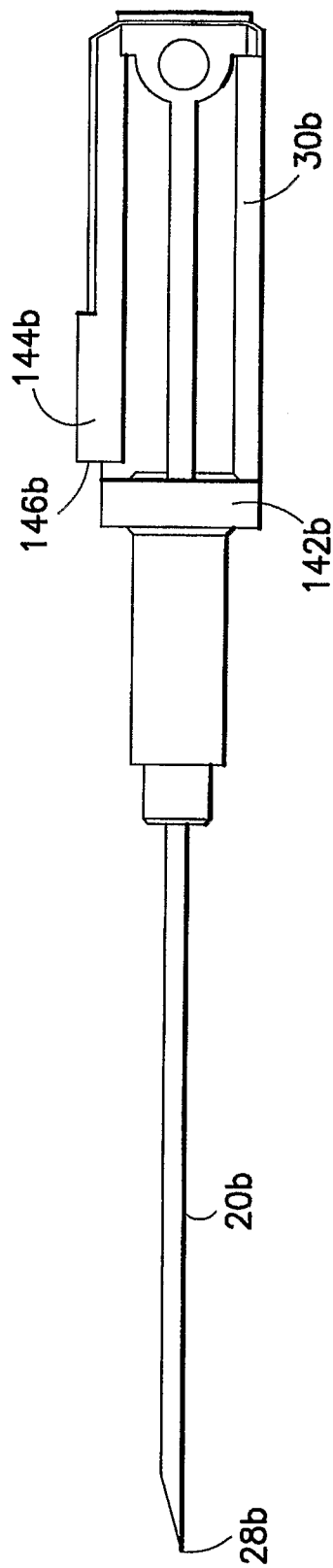
FIG. 23A is a side view of a hub of the needle device of FIG. 20.

Needle assembly 12*b* as shown in FIGS. 20-33 includes a hub 30*b* similar to that described above in connection with FIGS. 1-8. In particular, as shown in FIGS. 22 and 23A, the hub 30*b* includes a proximal end 32*b*, a distal end 34*b* and an internal passageway 42*b* extending between the ends. The first end 15*b* of flexible tubing 14*b* connects with the hub 30*b* in a manner as described above. Alternatively, portions of internal passageway 42*b* adjacent proximal end 32*b* may be dimensioned to receive the first end 15*b* of flexible tubing 14*b*. More particularly, the first end 15*b* of the tubing 14*b* may be telescoped into passageway 42*b* of the hub 30*b* and bonded in position adjacent the proximal end 32*b* of the hub 30*b*. Portions of the passageway 42*b* adjacent the distal end 34*b* of the hub 30*b* may also dimensioned for slidable receipt of the proximal end 22*b* of the needle cannula 20*b*.

External portions of the hub 30*b* may define a cylindrical portion 140*b* having a reduced diameter for mounting the drive member 80*b* thereover. A flange 142*b* defines a limit for proximal movement of the drive member 80*b* on the hub 30*b* and a limit for distal movement of the hub 30*b* relative to the shield 70*b*.

A release member in the form of a protrusion or button 144*b* extends distally outwardly from an external surface at the forward or distal end 34*b* of the hub 30*b*. The button 144*b* may be symmetrically aligned with the bevel-up orientation of the puncture tip 28*b* of the needle cannula 20*b*. The proximal end of the button 144*b* defines a surface at locking edge 146*b* which establishes an interference engagement with corresponding structure on the shield 70*b*, as will be described in more detail herein.

Figure 23B:
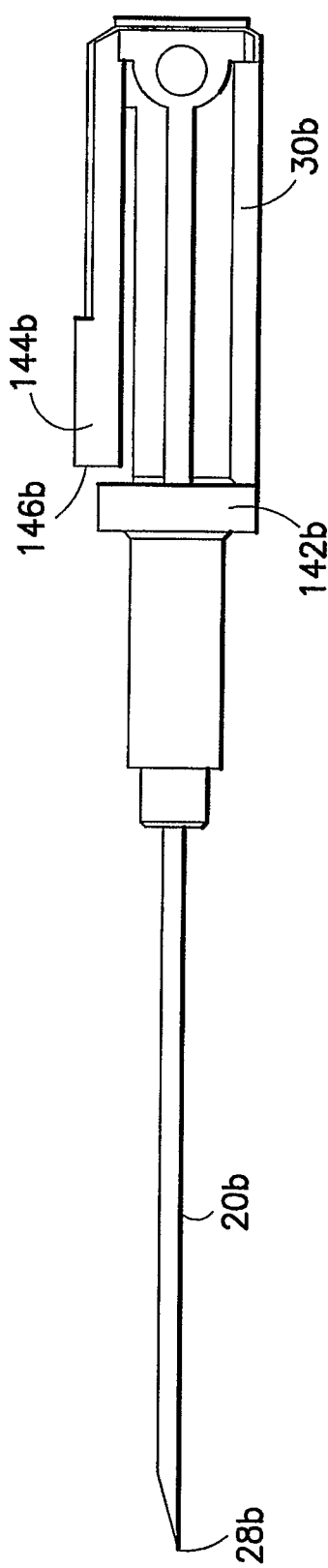
FIG. 23B is a side view of an alternate hub useful in the needle device of FIG. 20.
Figure 25:
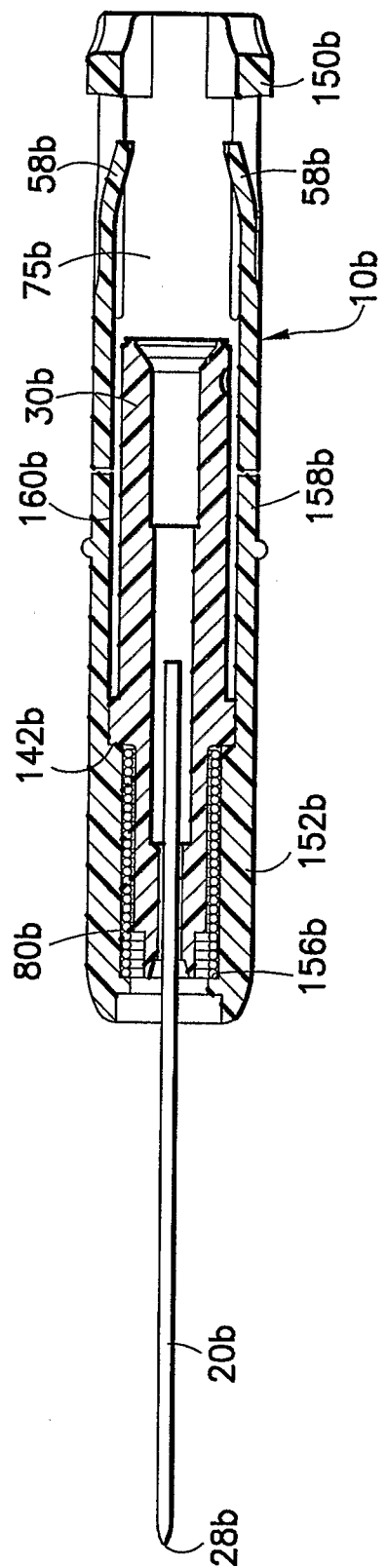
FIG. 25 is a top cross-sectional view of the needle device of FIG. 20, shown with the packaging cover removed and in the first position ready for use.
Figure 26:
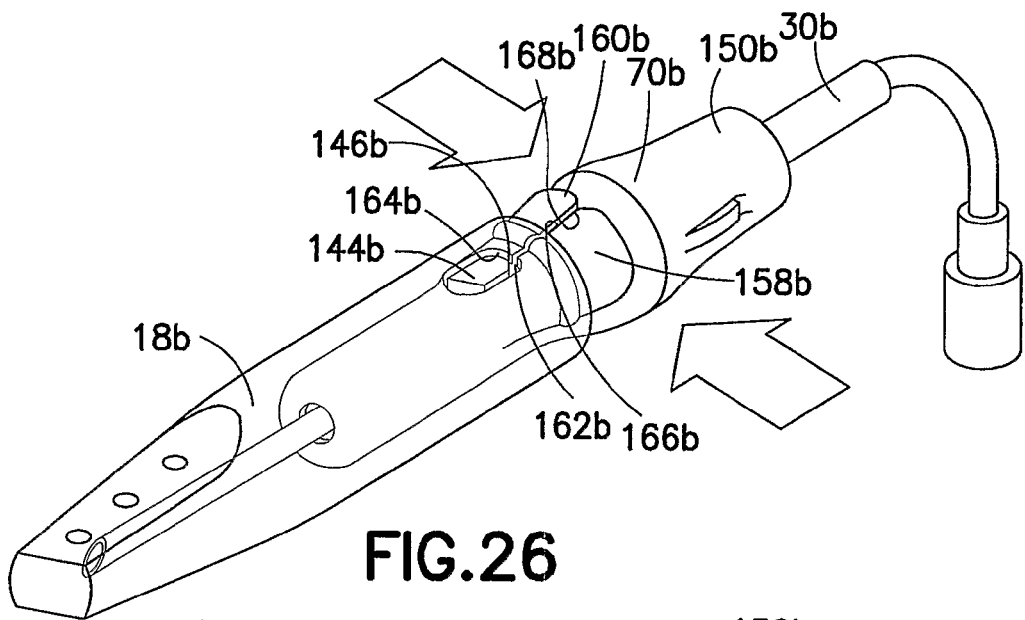
FIG. 26 is a perspective view showing the direction of forces for actuation of the shielding needle device of FIG. 20.
Figure 28:
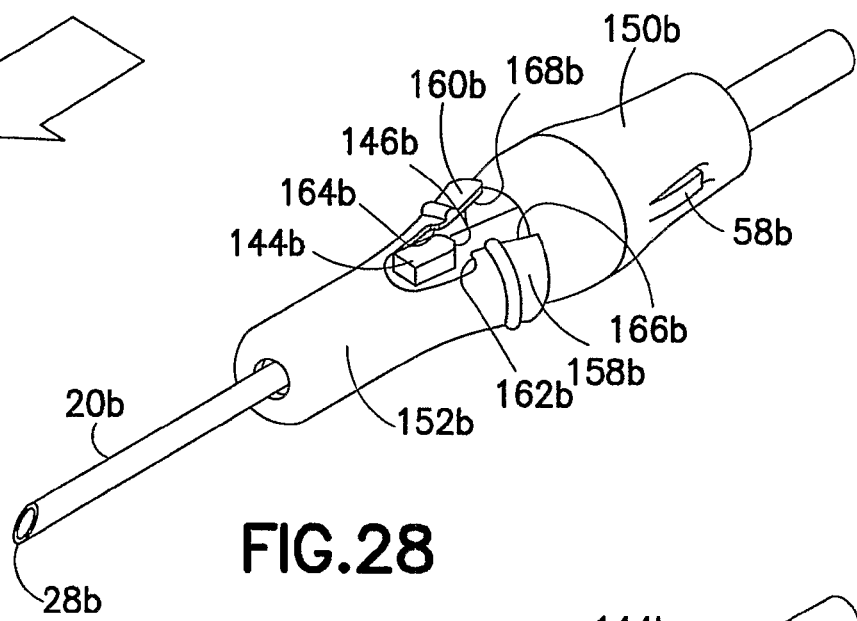
FIG. 28 is a perspective view showing of the shielding needle device of FIG. 20 in the first position after the user's fingers are released during activation.

FIG. 23B and FIG. 33 depict an alternate version of the hub 30*b* which is similar to that shown in FIG. 23A, but with the button 144*b* being radially flexible with respect to the body of the hub 30*b*. In particular, in the embodiment of the hub 30*b* shown in FIG. 23B and FIG. 33, the button is not merely a protrusion extending outwardly from the external surface of the hub 30*b*, but instead extends from an actuator arm of the hub 30*b* which is cantilevered to extend outwardly and distally from the proximal end of hub 30*b*, in a similar manner as is described with respect to the hub of the retractable needle assembly of U.S. Patent Application Publication No. 2003/0078540 to Saulenas, the disclosure of which is incorporated herein by reference. In this manner, button 144*b* is flexible radially inwardly. Such flexing may assist in movement of the hub 30*b* in the proximal direction during actation of the assembly, in that the button 144*b* can radially flex inwardly during retraction of the hub 30*b* to prevent any frictional or interference engagement with the shield 70*b*.

In the embodiment of FIGS. 20-33, the shield 70*b* may be provided as a barrel extending between proximal end 72*b* and distal end 74*b*, with an internal passageway 75*b* therethrough and a central opening 76*b* extending through the distal end 74*b* thereof. Desirably, the proximal end 72*b* and the distal end 74*b* define separate rearward and forward structures, respectively, which are unitarily formed, interconnected or otherwise attached together. For example, the proximal end of the shield 70*b* may be provided as a rearward shield structure 150*b*, in a cylindrical or barrel-like form. Rearward shield structure 150*b* has an internal diameter substantially the same as or slightly larger than the external diameter of the hub 30*b*, including the button 144*b*, and is therefore capable of accommodating hub 30*b* including the button 144*b* therethrough in a slidable manner. Rearward shield structure 150*b* is connected with forward shield structure 152*b* at a bridge section 154*b*. The bridge section 154*b* establishes the rearward shield structure 150*b* and the forward shield structure 152*b* as separate ends which are joined to each other.

The distal end 74*b* of the shield 70*b* defined by forward shield structure 152*b* defines an inwardly extending annular distal flange 156*b* with an inside diameter less than the outside diameter of the drive member 80*b*. Thus, distal flange 156*b* defines a distal stop for drive member 80*b* and enables drive member 80*b* to be compressed within the shield 70*b*. An internal portion of forward shield structure 152*b* may also define a fixed limit for distal movement of the hub 30*b* therein.

Needle assembly 12*b* includes structure adapted to maintain the hub 30*b* and drive member 80*b* in a pre-actuated state or position within the body of the shield 70*b* and to release or actuate the drive member 80*b*, in a similar manner as with release members 44 described above with reference to FIGS. 1-8. In particular, the forward shield structure 152*b* includes at least one, and preferably a pair of release tabs 158*b*, 160*b* on opposing lateral sides thereof. The release tabs 158*b*, 160*b* extend longitudinally along opposing sides of the forward shield structure 152*b*, such as in a proximal manner toward rearward shield structure 150*b*. The release tabs 158*b*, 160*b* are desirably integrally formed with the forward shield structure 152*b*, and may form structure similar to the release members 44 described above in connection with FIGS. 1-8. The release tabs 158*b*, 160*b* include distal edge surfaces 162*b*, 164*b*, respectively, as well as mating edges 166*b*, 168*b*, respectively. In a relaxed and unbiased state, the release tabs 158*b*, 160*b* naturally deflect outwardly, such as radially outwardly from the overall barrel structure of the shield 70*b*, with mating edges 166*b*, 168*b*, deflected away from each other. The release tabs 158*b*, 160*b* are flexible members with respect to forward shield structure 152b, and can be deflected inwardly to a biased state, such as radially inwardly to a position in which mating edges 166b and 168b substantially meet. In such a biased state of the release tabs 158b and 160b, the distal edge surfaces 162b and 164b of the opposing release tabs 158b and 160b form a perimeter edge of an opening or aperture 170b through the forward shield structure 152b. The aperture 170b thus formed is dimensioned and configured to receive button 144b, with the perimeter edge defined by the distal edge surfaces 162b and 164b configured for engaging proximal edge 146b of the button 144b.

In this manner, the hub 30b and the shield 70b can be maintained in a first position against the biasing force of the drive member 80b biasing the hub 30b and the shield 70b away from each other, i.e., biasing the hub 30b toward the proximal direction. External pressure applied between the opposing release tabs 158b and 160b of the shield 70b at the forward shield structure 152b in a radially inward direction deflects and biases the release tabs 158b and 160b against their relaxed state, causing mating edges 166b, 168b to meet, thereby establishing aperture 170b. The proximal edge 146b of button 144b is thereby in interference engagement with one or both of the distal edge surfaces 162b, 164b. As such, the drive member 80b is prevented from causing axial movement of the hub 30b and the shield 70b with respect to each other. Such pressure may also create a compressive force establishing a frictional engagement between the inner surfaces of the release tabs 158b, 160b and the external surface of the hub 30b, thus further holding the hub 30b within the shield 70b in the first position.

A packaging cover 18b is provided about the needle cannula 20b in engagement with a portion of the forward shield structure 152b, similar to that described above with respect to FIGS. 1-8. The packaging cover 18b is preferably in frictional engagement with the distal end 74b of the shield 70b at forward shield structure 152b, and is generally adapted to maintain the needle assembly 12b in the pre-actuated state with the hub 30b in the first position. Accordingly, the internal diameter of the packaging cover 18b is sized so as to exert a radially compressive force against the outer surface of the release tabs 158b, 160b so as to deflect and bias the release tabs 158b and 160b radially inwardly against their relaxed state. The outward pressure exerted by the release tabs 158b and 160b may be sufficient to frictionally maintain the packaging cover 18b in a frictional fit over forward shield structure 152b. Further, the packaging cover 18b may include structure for interlocking engagement with a portion of forward shield structure 152b in a similar manner as described above with reference the release members 44 of FIGS. 1-8, such that when the release tabs 158b and 160b are grasped during use, any such interlocking engagement with the packaging cover 18b is released.

Figure 27:
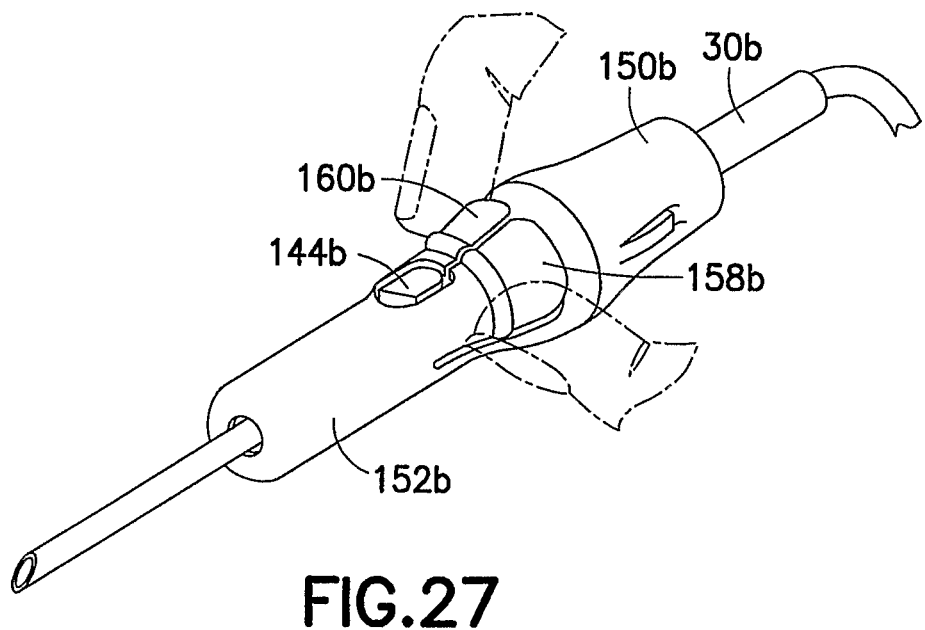
FIG. 27 is a perspective view showing of the shielding needle device of FIG. 20 with the packaging cover removed and with a user's fingers maintaining the needle device in the first position with the needle cannula exposed for use.
Figure 21:
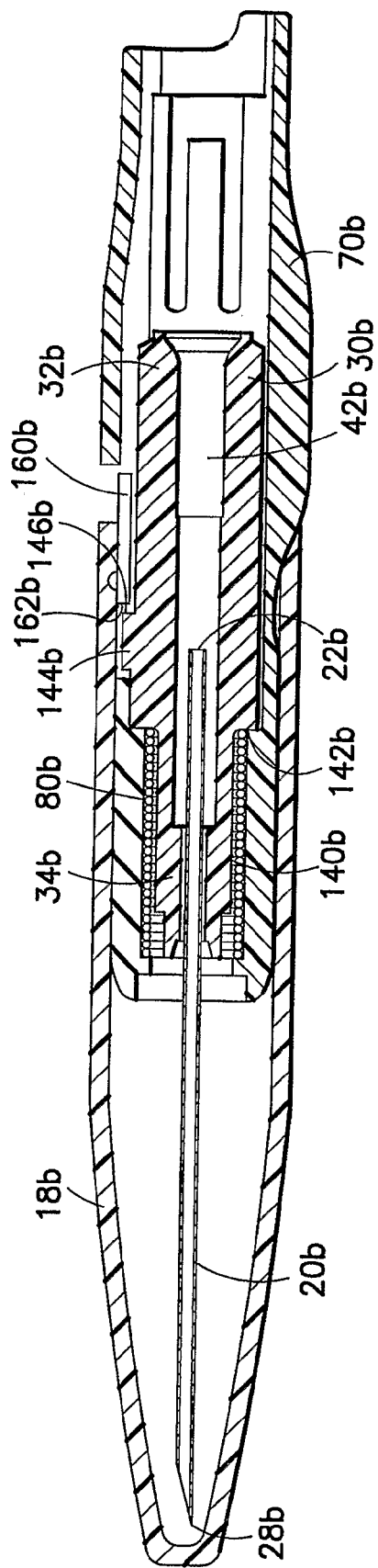
FIG. 21 is a longitudinal cross-sectional view of the needle device of FIG. 20.

To use the needle assembly 12b of the embodiment set forth in FIGS. 20-33, the user generally grasps the assembly at opposing sides thereof to apply external pressure between opposing surfaces of the release tabs 158b, 160b in the direction shown in FIG. 27. As the user applies external force through inwardly or radially directed pressure to the release tabs 158b, 160b, the packaging cover 18b is removed from the forward shield structure 152b at the distal end 74b of the shield 70b by the user. The user maintains the external force of the inwardly directed pressure applied to the release tabs 158b, 160b, which maintains the mating edges 166b, 168b in a position substantially meeting each other. As such, button 144b is maintained within the aperture 170b, with the proximal edge 146b of button 144b in interference engagement with distal edge surfaces 162b, 164b. In this manner, the pressure applied by the user maintains the interference engagement between the release tabs 158b, 160b and the release member of button 144b, thereby maintaining the hub 30b in the first position and counteracting the proximally-directed biasing force of the drive member 80b against the hub 30b. The radial pressure applied to the release tabs 158b, 160b generally takes the place of the removed packaging cover 18b for maintaining the hub 30b in the first position and counteracting the biasing force of the drive member 80b.

The user may then urge the puncture tip 28b at distal end 24b of the needle cannula 20b into a targeted blood vessel of a patient in order to conduct a blood collection procedure or other procedure as desired. After proper positioning, when the user releases the applied pressure applied to the release tabs 158b, 160b, the release tabs 158b, 160b deflect outwardly to their relaxed unbiased state, with mating edges 166b, 168b moving away from each other. At this point, the interference engagement between the proximal edge 146b of the button 144b and the distal edge surface 162b, 164b is released. As such, the drive member 80b is free to exert a biasing force between the hub 30b and the shield 70b, with the drive member 80b propelling the hub 30b proximally through the rearward shield structure 150b. During an actual blood collection procedure, the compressive force of the drive member 80b is insufficient to withdraw the needle cannula 20b from the patient, and instead the shield 70b will move distally and terminate when the distal end 74b of the safety shield 70b contacts the skin of the patient. The drive member 80b still exerts a biasing force between the shield 70b and the hub 30b, but this force is resolved by the frictional force that acts on the needle cannula 20b, as a result of being in the blood vessel of the patient. The user may then proceed to complete the blood collection procedure, for example using evacuated blood collection tubes or a syringe.

Figure 29:
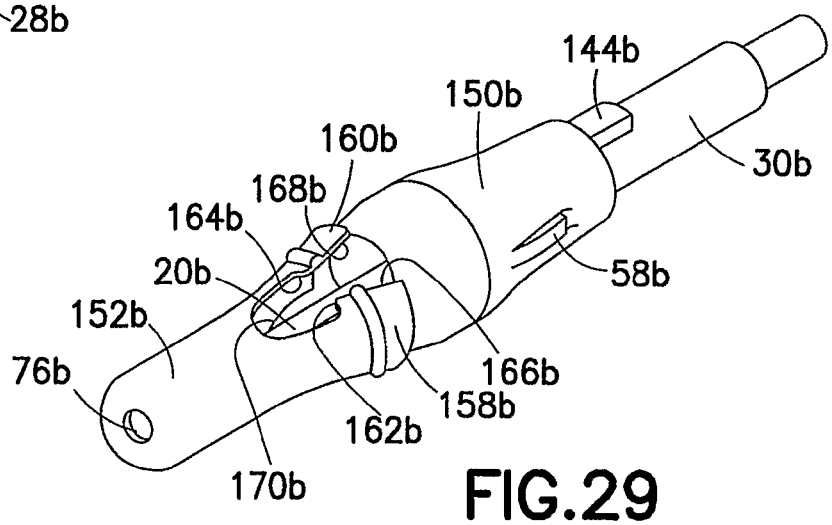
FIG. 29 is a perspective view showing of the shielding needle device of FIG. 20 in the second position with the shield encompassing the needle cannula.
Figure 30:
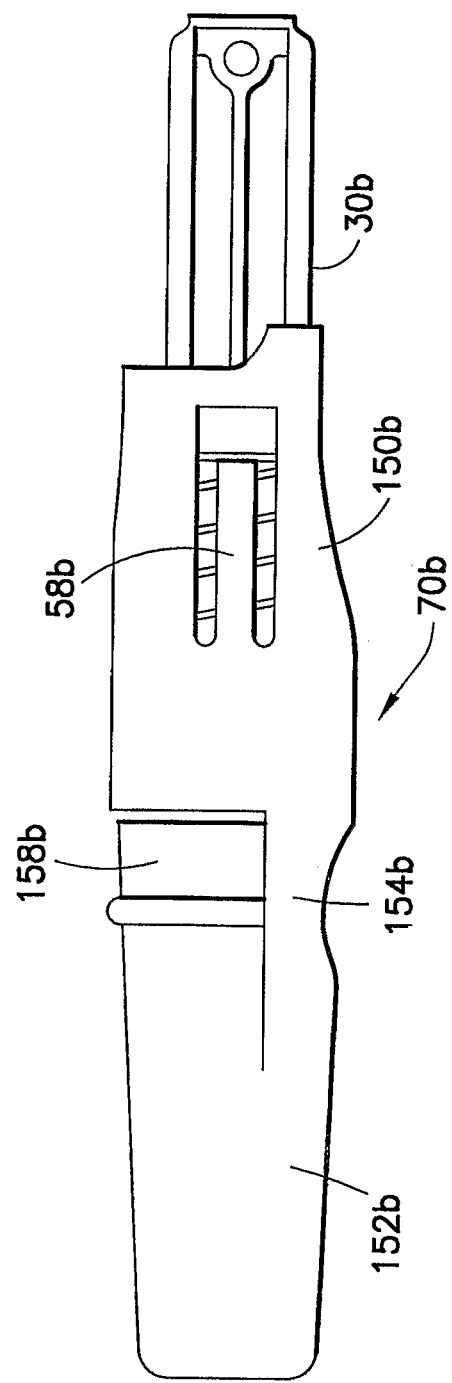
FIG. 30 is a side view of the shielding needle device of FIG. 20 shown in the second position with the shield encompassing the needle cannula.

The user then proceeds to remove the needle assembly 12b from the blood vessel of the patient. As the needle cannula 20b is removed from the blood vessel of the patient, the safety shield 70b is urged by the drive member 80b to move closer to the distal end 24b of the needle cannula 20b. As the needle cannula 20b is fully removed from the patient's blood vessel, the safety shield 70b is urged by the drive member 80b to fully encompass the needle cannula 20b, as generally depicted in FIGS. 29 and 30. The drive member 80b exerts a biasing force that will aid in preventing the re-emergence of the puncture tip 28b from the central opening 76b in the distal end 74b of the safety shield 70b.

Figure 31:
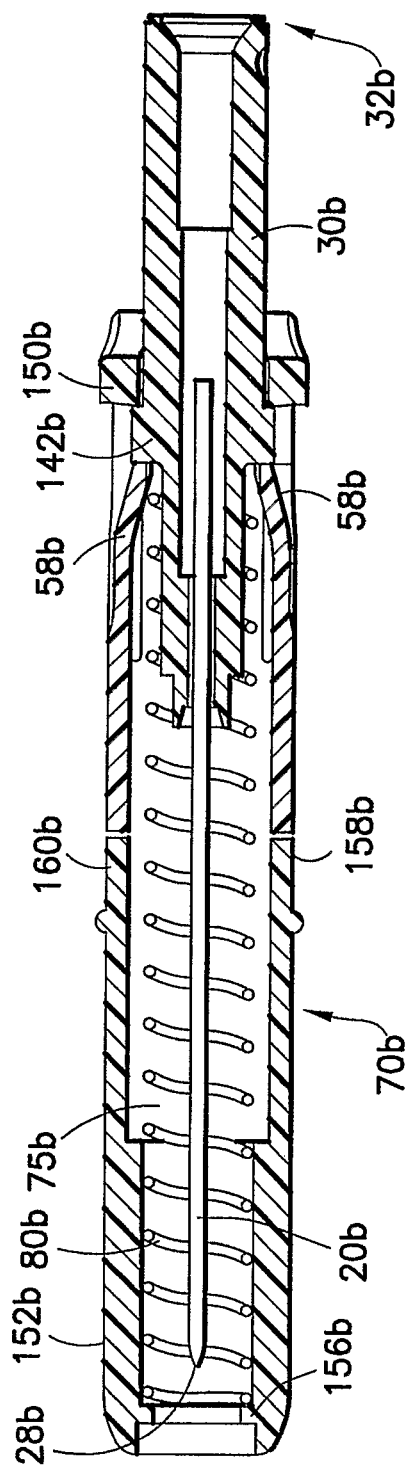
FIG. 31 is a top cross-sectional view of the needle device of FIG. 20, shown in the second position with the shield encompassing the needle cannula.
Figure 32:
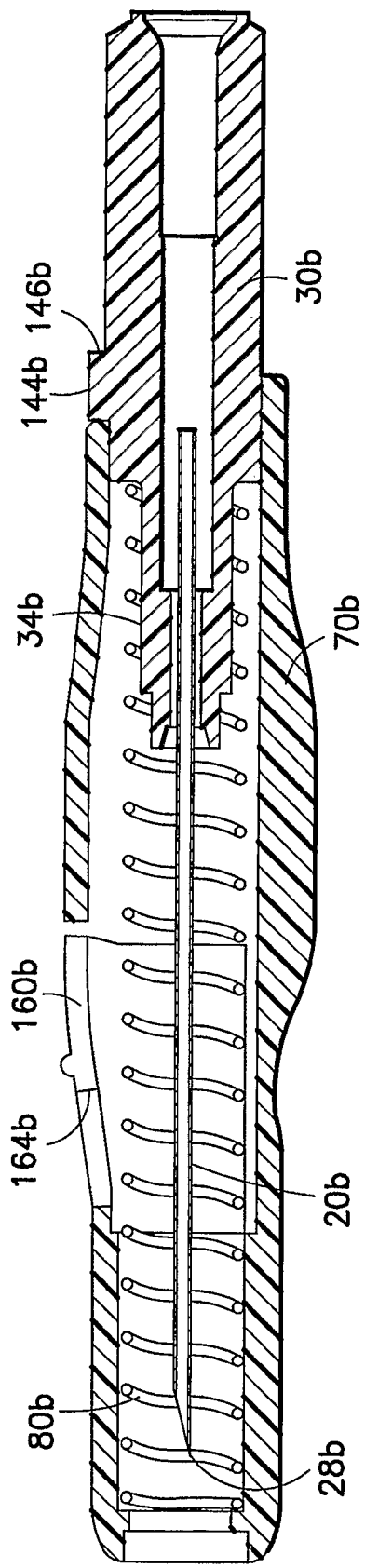
FIG. 32 is a longitudinal cross-sectional view of the needle device of FIG. 20, shown in the second position with the shield encompassing the needle cannula.

The safety shield 70b and the hub 30b may further include interengaging structure for interfering engagement therebetween for securing the safety shield 70b in the extended position to prevent a return movement once the needle assembly 12b has been actuated. For example, the safety shield 70b may include external locking structure in a similar manner as described above with respect to FIGS. 1-8. For example, the rearward shield structure 150b may include resiliently deflectable locking fingers or tabs 58b that are cantilevered proximally and inwardly from opposed locations. As shown in FIG. 31, each locking finger or tab 58b is adapted to engage a portion of the hub 30b when the hub 30b is in the second position with the needle cannula safely encompased within shield 70b. Needle assembly 12b can thereafter be appropriately discarded.

The particular elements of the needle assembly can be manufactured of any known materials. Desirably, the hub, the shield, and the packaging cover are individually molded from plastic materials such as polycarbonate, polypropylene, polyethylene, acrylic, polystyrene and ABS. Preferably the hub and/or the shield are molded from a transparent or translucent material to enable observation of blood or other fluid flowing through the hub during use of the device.

The shielding feature of the present invention is passively actuated upon normal usage of the device. In particular, upon removal of the packaging cover prior to insertion, the safety feature is primed and charged, ready for shielding the needle once the user releases the opposing finger tabs. Moreover, in some instances, the needle assembly may be dropped or knocked from the hand of the user before, during, or after use. The shielding feature described above will commence automatically when the needle assembly is dropped or knocked from the user's hand. Thus, the automatic shielding may be triggered by the intentional or unintentional release of the finger tabs by the user.

Additionally, a user, such as a medical practitioner, does not always enter the targeted blood vessel during the first venipuncture attempt. However, a medical practitioner typically retains a close grip on the needle assembly until the targeted blood vessel has been entered. In this instance, the continued gripping of the finger tabs will prevent the needle assembly from shielding until the targeted blood vessel has been punctured. The second attempt at accessing a targeted blood vessel generally is a very low risk procedure in which the user's hand is spaced considerably from the puncture tip of the needle cannula. Thus, the blood collection set does not involve the inconvenience of having to use a new blood collection set following each unsuccessful venipuncture attempt.

While the needle assembly of the present invention has been described in terms of various embodiments for use in connection with a blood collection system, it is further contemplated that the needle assembly could be used with other medical procedures, such as in conjunction with a conventional intravenous infusion set, which are well-known in the art for use with needle assemblies. While the present invention is satisfied by embodiments in many different forms, there is shown in the drawings and described herein in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

The invention claimed is:

1. A safety needle device comprising:
a hub including a passageway extending therethrough and a needle cannula having a puncture tip extending from a forward end thereof;
a shield member in telescoping association with the hub, at least one of the hub and the shield member adapted for relative telescopic movement with respect to the other between a first position in which the puncture tip of the needle cannula is exposed from a forward end of the shield member and a second position in which the puncture tip of the needle cannula is encompassed within the shield member;
a drive member disposed between the hub and the shield member and capable of biasing the hub and the shield member telescopically away from each other, and
a releasable packaging cover disposed about the puncture tip of the needle cannula, the packaging cover adapted to apply pressure to at least one of the hub and the shield member to provide an engagement therebetween, thereby preventing the drive member from biasing the hub and the shield member telescopically away from each other, and
wherein pressure applied by a user directly to at least one of the hub and the shield member establishes a frictional engagement therebetween, preventing the drive member from biasing the hub and the shield member axially away from each other.

2. A safety needle device as in claim 1, wherein the shield member includes a forward end and a rearward end defining a passageway extending substantially therebetween with the hub disposed within the passageway of the shield member and being movable relative to the shield member between the first position wherein the puncture tip of the needle cannula projects from the forward end of the shield member and a second position wherein the puncture tip of the needle cannula is encompassed by the shield member,
wherein the hub further comprises a release member, and the shield member further comprises at least one release tab adapted for engagement with the release member of the hub and adapted to deflect radially outwardly from the shield member when in a relaxed, unbiased state,
wherein pressure maintains the at least one release tab in the biased state in interference engagement with at least a portion of the release member of the hub, thereby maintaining the hub in the first position against the bias of the drive member, and
wherein sufficient release of the pressure from the at least one release tab permits the at least one release tab to move to the unbiased state out of interference engagement with the release member, allowing the drive member to move the hub toward the second position wherein the puncture tip of the needle cannula is encompassed by the shield member.

3. A safety needle device as in claim 2, wherein the release member extends from an external surface of the hub forming a button, and wherein the at least one release tab extends longitudinally from the rearward end of the shield member.

4. A safety needle device as in claim 3, wherein the at least one release tab comprises opposing release tabs disposed on opposing lateral sides of the shield member, the opposing release tabs cooperatively defining an opening for receiving the button in an interference engagement in the biased state of the release tabs.

5. A safety needle device as in claim 1, wherein application of pressure by a user to at least one of the hub and the shield member allows for release of the packaging cover from the needle device and maintains the engagement between the hub and the shield member to prevent the drive member from biasing the hub and the shield member telescopically away from each other.

6. A safety needle device as in claim 5, wherein the hub or the shield member includes at least one release member disposed at least partially within the packaging cover and adapted to flex radially inward toward a central longitudinal axis of the needle device upon application of pressure thereto, allowing passive release of the packaging cover from the hub or the shield member.

7. A safety needle device as in claim 1, wherein the hub includes a dorsal member extending from an external surface thereof, and wherein the shield member includes a grip structure extending dorsally therefrom adapted for corresponding engagement with the dorsal member at the external surface of the hub when the shield member is in a first retracted position; and
wherein pressure applied between the grip structure of the shield member and the dorsal member of the hub prevents the drive member from biasing the hub and the shield member telescopically away from each other.

8. A safety needle device as in claim 7, wherein the shield member telescopes within the passageway of the hub and the grip structure extends dorsally from the shield member toward the dorsal member of the hub, wherein pressure applied between the grip structure of the shield member and the dorsal member of the hub establishes frictional engagement therebetween, thereby maintaining the shield member in a retracted position within the passageway of the hub against the bias of the drive member with the puncture tip of the needle cannula exposed, and wherein release of the pressure between the grip structure of the shield member and the dorsal member of the housing releases the frictional engagement, allowing the drive member to bias the shield member toward an extended position in which the puncture tip of the needle cannula is encompassed within the shield member.

9. A safety needle device as in claim 1, wherein pressure applied by a user between corresponding surfaces of the hub and the shield member provides an interference engagement therebetween, preventing the drive member from biasing the hub and the shield member telescopically away from each other.

10. A safety needle device as in claim 1, wherein the drive member comprises a coil spring.

11. A safety needle device comprising:
a hub including a passageway extending therethrough and a needle cannula having a puncture tip extending from a forward end thereof, the hub including a dorsal member extending from an external surface thereof;
a shield adapted for telescopic movement between a retracted position exposing the puncture tip of the needle cannula and an extended position covering the puncture tip of the needle cannula, the shield including a grip structure extending dorsally therefrom adapted for corresponding engagement with the dorsal member of the hub when the shield is in the retracted position; and
a drive member extending between the hub and the shield and biasing the shield toward the extended position;
wherein pressure applied directly to the grip structure of the shield or the dorsal member of the hub establishes frictional engagement therebetween, thereby maintaining the shield in the retracted position against the bias of the drive member.

12. A needle device as in claim 11, wherein the dorsal member of the hub comprises a generally planar spine extending dorsally from the external surface of the hub in a plane corresponding to a longitudinal axis defined by the needle cannula, and wherein the grip structure comprises generally planar structure for corresponding engagement with the spine of the hub.

13. A needle device as in claim 12, wherein the grip structure comprises a pair of flexibly resilient planar leafs extending from a forward end of the shield in a plane corresponding to the longitudinal axis defined by the needle cannula, the pair of planar leafs being spaced from each other to define an opening therebetween for accommodating the spine of the hub.

14. A needle device as in claim 13, wherein the pair of planar leafs and the spine include corresponding structure adapted for interference engagement therebetween when pressure is applied between t he pair of planar leafs and the spine.

15. A needle device as in claim 11, further comprising a packaging cover releasably covering the forward end of the puncture tip when the shield is in the retracted position and maintaining the shield in the retracted position against the bias of the drive member.

16. A needle device as in claim 15, wherein the packaging cover applies pressure between the grip structure of the shield and the dorsal member of the hub to maintain the shield in the retracted position against the bias of the drive member.

17. A needle device as in claim 11, wherein at least a portion of the shield extends coaxially within the passageway of the hub with a forward end extending from a forward end of the hub, and wherein the grip structure extends dorsally from the forward end of the shield.

18. A needle device as in claim 17, wherein the drive member comprises a compression spring extending within the passageway of the hub and biasing against a rearward end of the shield.

19. A needle device as in claim 11, wherein release of the pressure between the grip structure of the shield and the dorsal member of the hub releases the frictional engagement, allowing the drive member to bias the shield toward the extended position.

20. A needle device as in claim 11, wherein the hub and the shield include interengaging structure for interfering engagement therebetween when the shield is in the extended position to prevent a return movement of the shield to the retracted position.

21. A needle device as in claim 11, wherein the hub includes a pair of wings extending laterally from opposing sides thereof in fixed relation to the hub, and wherein corresponding engagement of the dorsal member of the hub and the grip structure of the shield form a dorsal grasping structure when the shield is in the retracted position, the dorsal grasping element having a profile larger than the pair of wings on the hub.

22. A needle device as in claim 11, wherein the hub further comprises structure for attachment to a medical device.

23. A safety needle device comprising:
a hub including a passageway extending therethrough with a needle cannula having a puncture tip extending from a forward end thereof, the hub including a dorsal member extending from an external surface thereof;
a shield adapted for telescopic movement between a retracted position adjacent said hub in which the puncture tip of the needle cannula is exposed and an extended position covering the puncture tip of the needle cannula, the shield including grip structure extending dorsally from an external surface thereof; and
a cover releasably covering the forward end of the puncture tip and maintaining the shield in the retracted position against a biasing force biasing the shield toward the extended position;
wherein pressure applied directly to the grip structure of the shield or the dorsal member of the hub establishes frictional engagement therebetween, thereby maintaining the shield in the retracted position against the biasing force upon removal of the cover, and wherein removal of the cover and release of the external pressure between the grip structure and the shield releases the frictional engagement, thereby biasing the shield toward the extended position.

24. A needle device as in claim 23, wherein the cover applies pressure between the grip structure of the shield and the dorsal member of the hub to maintain the shield in the retracted position against the biasing force.

25. A needle device as in claim 23, further comprising a compressing spring extending within the passageway of the hub and extending between the hub and the shield for biasing the shield toward the extended position.

\* \* \* \* \*